United States Patent
Murai et al.

(10) Patent No.: US 8,348,463 B2
(45) Date of Patent: Jan. 8, 2013

(54) ILLUMINATION DEVICE AND PRODUCING METHOD THEREOF

(75) Inventors: Hideyuki Murai, Kobe (JP); Naoki Nishimori, Kusatsu (JP); Kosuke Sugiyama, Ayabe (JP); Akira Matsui, Joyo (JP); Kenji Homma, Joyo (JP); Jun Ota, Kizugawa (JP); Sayuki Nakada, Otsu (JP); Rie Masuda, Nara (JP)

(73) Assignee: Omron Corporation, Kyoto (JP)

( * ) Notice: Subject to any disclaimer, the term of this patent is extended or adjusted under 35 U.S.C. 154(b) by 203 days.

(21) Appl. No.: 12/981,381

(22) Filed: Dec. 29, 2010

(65) Prior Publication Data

US 2011/0170293 A1   Jul. 14, 2011

(30) Foreign Application Priority Data

Dec. 29, 2009  (JP) ................... 2009-299154

(51) Int. Cl.
*F21S 4/00* (2006.01)
*H01J 9/00* (2006.01)

(52) U.S. Cl. .................. 362/249.03; 362/97.3; 362/235; 362/245; 445/24; 445/22

(58) Field of Classification Search ............ 362/311.01–311.05, 543–549, 555, 800, 249.01–249.03, 362/235–245, 97.3; 445/1, 23; 438/26–28, 438/106
See application file for complete search history.

(56) References Cited

FOREIGN PATENT DOCUMENTS

| JP | 10-320538 | 12/1998 |
|---|---|---|
| JP | 2006-179387 | 7/2006 |
| JP | 2006-222413 | 8/2006 |
| JP | 2008-139708 | 6/2008 |
| JP | 2009-54293 | 3/2009 |
| JP | 2009-146841 | 7/2009 |

OTHER PUBLICATIONS

Patent Abstracts of Japan for patent application with Publication No. 2006-222413, Publication Date: Aug. 24, 2006, 1 page.
Mechanical English translation for Japanese patent application with Publication No. 2006-222413, Publication Date: Aug. 24, 2006, 71 pages.
Patent Abstracts of Japan for patent application with Publication No. 10-320538, Publication Date: Dec. 4, 1998, 1 page.
Mechanical English translation for Japanese patent application with Publication No. 10-320538, Publication Date: Dec. 4, 1998, 10 pages.
Patent Abstracts of Japan for patent application with Publication No. 2006-179387, Publication Date: Jul. 6, 2006, 1 page.

(Continued)

*Primary Examiner* — Nimesh Patel
*Assistant Examiner* — Donald Raleigh
(74) *Attorney, Agent, or Firm* — Osha Liang LLP

(57) ABSTRACT

An illumination device has a board, a plurality of light emitting elements that are mounted on the board, the plurality of light emitting elements being disposed such that a light irradiation direction of each light emitting element becomes substantially perpendicular to the board, and a plurality of lenses. Each of the plurality of lens is paired with one of the plurality of light emitting elements. A relative positional relationship between the light emitting element and the lens in each pair varies according to a position on the board in which the corresponding light emitting element is disposed.

19 Claims, 26 Drawing Sheets

OTHER PUBLICATIONS

Mechanical English translation of Japanese patent application with Publication No. 2006-179387, Publication Date: Jul. 6, 2006, 15 pages.
Patent Abstracts of Japan for patent application with Publication No. 2009-054293, Publication Date: Mar. 12, 2009, 1 page.
Mechanical English translation for patent application with Publication No. 2009-054293, Publication Date: Mar. 12, 2009, 14 pages.
Patent Abstracts of Japan, for patent application with Publication No. 2008-139708, Publication Date: Jun. 19, 2008, 1 page.
Mechanical English translation for patent application with Publication No. 2008-139708, Publication Date: Jun. 19, 2008, 11 pages.
Patent Abstracts of Japan for patent application with Publication No. 2009-146841, Publication Date: Jul. 2, 2009, 1 page.
Mechanical English translation of Japanese patent application with Publication No. 2009-146841, Publication Date: Jul. 2, 2009, 9 pages.

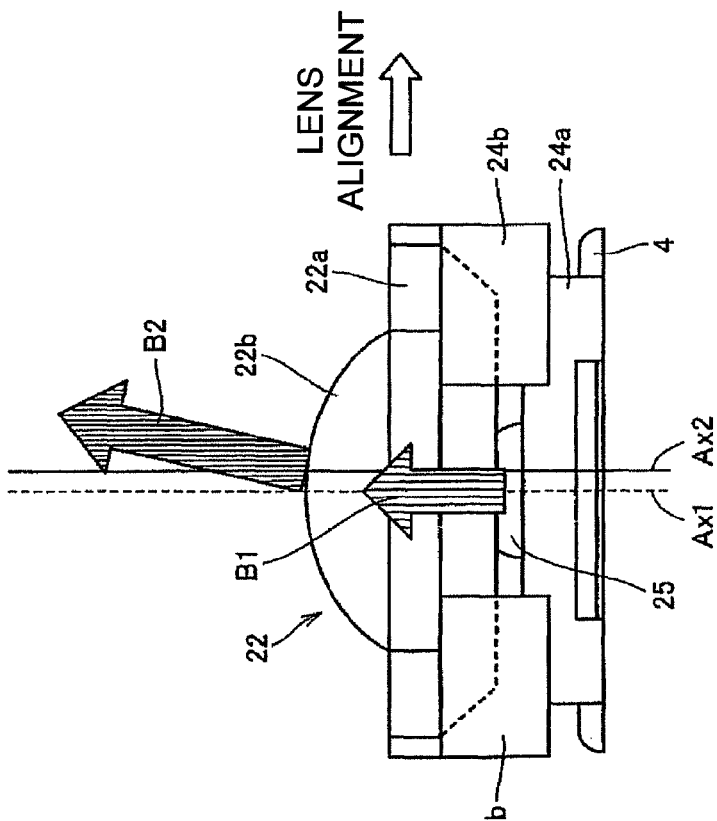
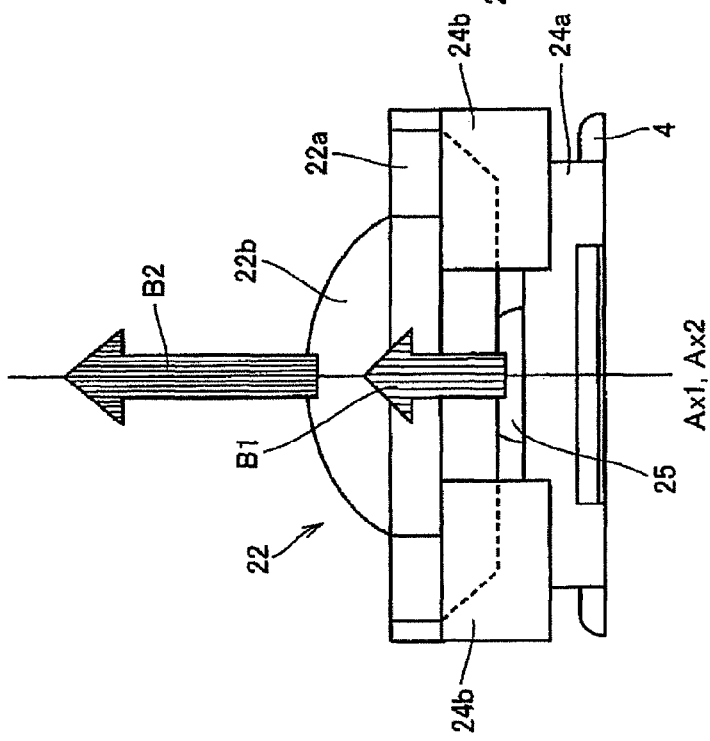
FIG. 5A
FIG. 5B

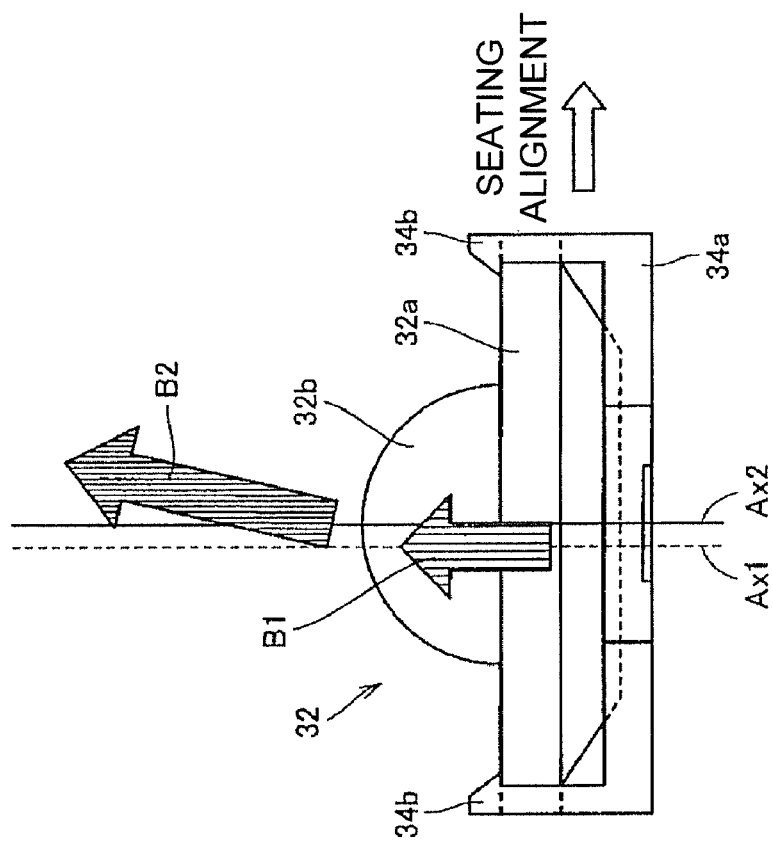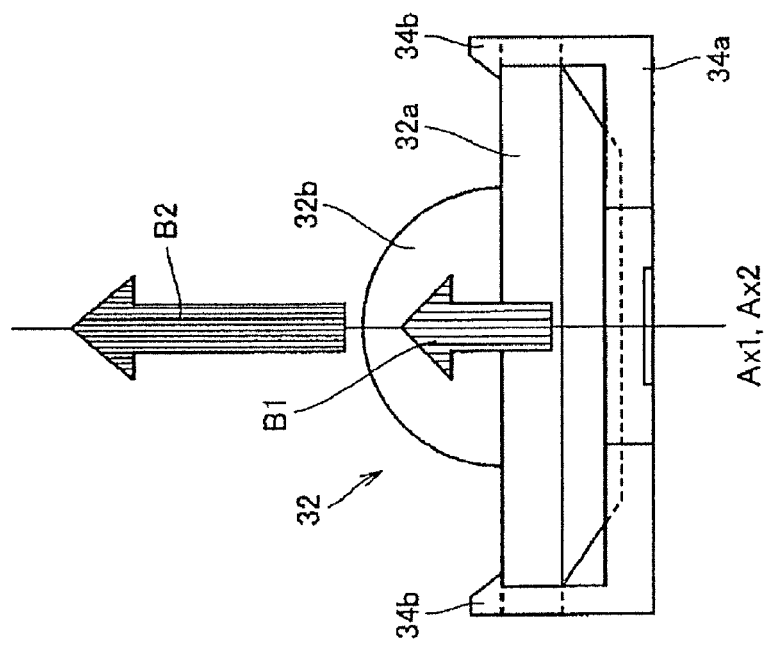

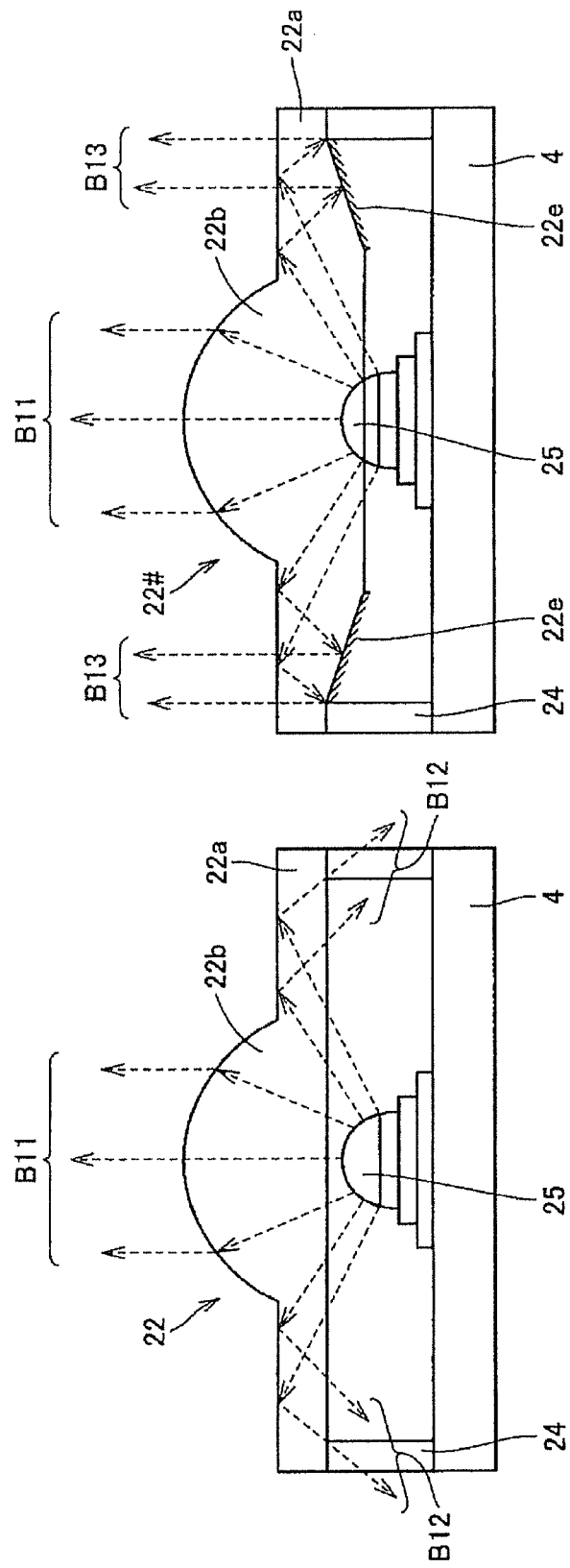

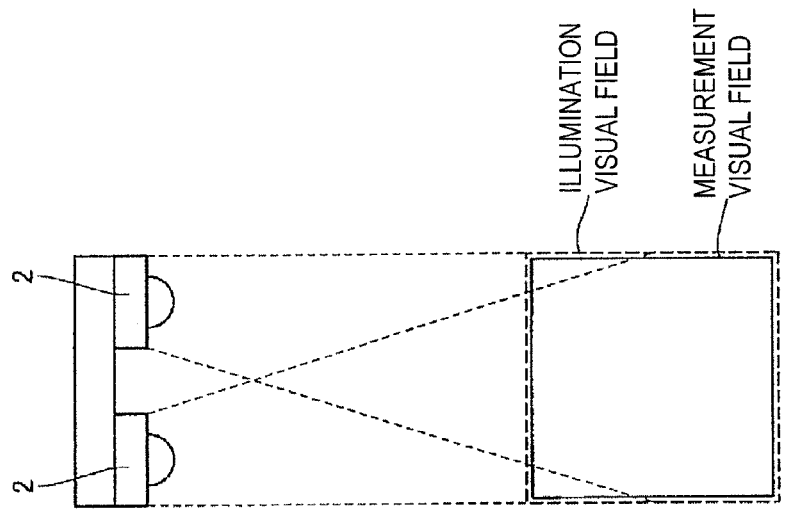
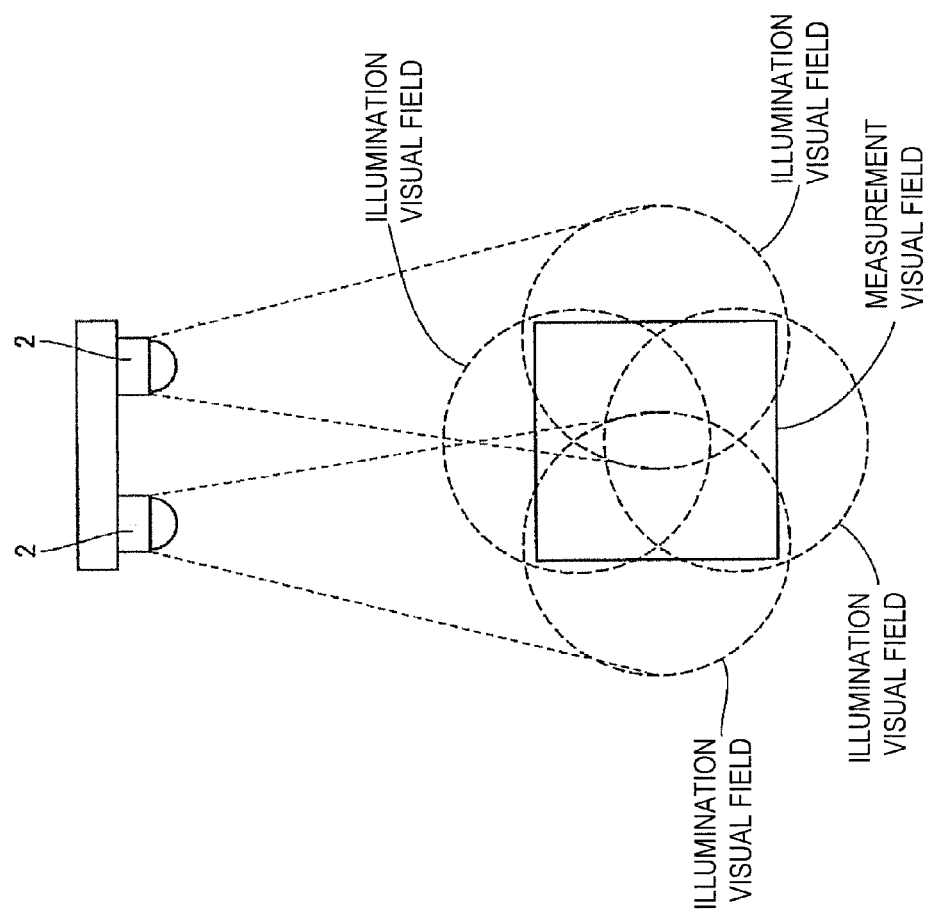

ILLUMINATION DEVICE AND PRODUCING METHOD THEREOF

BACKGROUND OF THE INVENTION

1. Technical Field

The present invention relates to an illumination device suitable for an image processing device and a method for producing the illumination device.

2. Related Art

Conventionally, various image processing techniques are used in the field of FA (Factory Automation). For example, a visual sensor device disclosed in Japanese Unexamined Patent Publication No. 10-320538 is an inspection device that is aimed at wide range of objects from a small object such as an electronic component to a large object such as an automobile. In such visual sensors, the object is imaged to obtain image data and a determination whether the object is non-defective or defective is made by performing image recognition processing to the image data.

Japanese Unexamined Patent Publication No. 10-320538 discloses a configuration in which a camera used to obtain an image of the object and a light source used to illuminate the object during the imaging are integrated.

Recently, an illumination device in which a light emitting element such as an LED (Light Emitting Diode) whose power consumption is less than ever before is used is rapidly developed because of an environmental problem. The LED is used as a light source even in the visual sensor disclosed in Japanese Unexamined Patent Publication No. 10-320538. For example, the following conventional techniques are used as the illumination device in which the LED is used.

In a light irradiation device disclosed in Japanese Unexamined Patent Publication No. 2006-179387, plural LEDs are disposed such that each optical axis has a predetermined oblique angle with respect to an axis line direction of a ring-shaped main body, the LEDs located on the same circumference have the same directivity in the plural LEDs, at least one pair of adjacent LEDs located on the same circumference have a different directivity, which allows lighting to be switched in each plural LED located on the same circumference. Therefore, a light irradiation range can be adjusted.

Additionally, in the light irradiation device disclosed in Japanese Unexamined Patent Publication No. 2006-179387, part of a flexible wiring board is cut out, and a cut-out piece is joined to form a cut-head conical concave surface, which allows an irradiation angle to be adjusted.

An LED illumination device disclosed in Japanese Unexamined Patent Publication No. 2009-054293 includes plural LEDs with which an object is illuminated, a board on which the LEDs are mounted, and a driving mechanism that drives the board to change optical axis directions of the LEDs. Therefore, brightness of the illumination is stabilized without increasing the number of LEDs.

In a ring type illumination device disclosed in Japanese Unexamined Patent Publication No. 2008-139708, plural LED rows are concentrically provided, plural optical members are concentrically provided according to each LED row such that illumination modes with the LED rows with respect to a workpiece differ from each other, and optical members are continuously integrated. Therefore, one ring type illumination device can respond to plural kinds of objective lenses and workpieces.

In an LED illumination device disclosed in Japanese Unexamined Patent Publication No. 2009-146841, a base portion includes plural projections that are projected upward from an upper surface, plural LEDs are mounted on an upper surface of an LED board, through-holes are made in the LED board as many as the projections such that a leading end of the projection penetrates through the through-hole, the leading end of the projection penetrates through the corresponding through-hole to position and dispose the LED board on the upper surface side of the base portion, insertion holes are made as many as the projections such that the leading end of the projection penetrating through the through-hole is inserted in the insertion hole, and the leading end of the projection is inserted in the corresponding insertion hole to position and dispose the projection on the upper surface side of the LED board, the LED illumination device including a lens holder that has a reflecting part in which a reflecting surface is formed at each LED, the reflecting surface standing upward from the upper surface of the LED board while surrounding one LED in the vicinity of the upper surface of the LED board.

As described above, because the visual sensor is intended to measure various objects, according to one or more embodiments of the present invention, many variations (product group) are lined up for an illumination visual field and a work distance (hereinafter also referred to as "WD") such that the light source (that is, illumination) can be applied to any object.

However, in the visual sensor disclosed in Japanese Unexamined Patent Publication No. 10-320538, because the illumination visual field and the WD cannot be adjusted, it is necessary to prepare chassis and the LEDs according to the number of variations, which results in cost increase.

In the light irradiation device disclosed in Japanese Unexamined Patent Publication No. 2006-179387, it is necessary to prepare the flexible wiring boards according to the number of variations, which results in cost increase. It is also necessary to obliquely dispose each LED with respect to the irradiation direction of the light irradiation device, which results in an angle being relatively hardly set and adjusted in order to realize the desired illumination visual field and WD.

In the configuration of the LED illumination device disclosed in Japanese Unexamined Patent Publication No. 2009-054293, because the illumination visual field and the WD are mechanically adjusted, a structure is relatively complicated, which results in cost increase.

In the ring type illumination device disclosed in Japanese Unexamined Patent Publication No. 2008-139708, it is necessary to prepare annular lenticular lenses according to the number of variations, which results in cost increase.

In the LED illumination device disclosed in Japanese Unexamined Patent Publication No. 2009-146841, it is necessary to prepare the base portions including the plural projections, designed according to the illumination visual fields and WDs, according to the number of variations, which results in cost increase. Additionally a position deviation cannot be corrected when the board is mounted on the LED because the plural lenses are retained in one lens holder, which results in a relatively positional accuracy between the LED and the lens being degraded.

SUMMARY

One or more embodiments of the present invention provides an illumination device lineup having many variations that respond to various illumination visual fields and work distances while the cost is controlled. One or more embodiments of the present invention provides a producing method for implementing the illumination device having the many variations.

In accordance with one aspect of the invention, there is provided an illumination device including: a board; a plurality of light emitting elements that are mounted on the board, the plurality of light emitting elements being disposed such that a light irradiation direction of each light emitting element becomes substantially perpendicular to the board; and a plurality of lenses that are disposed such that each lens is paired with one of the plurality of light emitting elements, wherein a relatively positional relationship between the light emitting element and the lens in each pair varies according to a position on the board in which the corresponding light emitting element is disposed.

"The relatively positional relationships differ from one another" means that the relatively positional relationship in a certain pair differs from the relatively positional relationship in at least another pair. Therefore, occasionally the relatively positional relationships are matched with each other between the two pairs.

Preferably, an optical axis of the lens in each pair is disposed while deviated to a direction that should be irradiated with light from the light emitting element with respect to a state in which the optical axis is positioned to an axis in the light irradiation direction of the corresponding light emitting element.

Preferably, the board includes an opening through which pieces of light, generated by reflection of the pieces of light from the plurality of light emitting elements in an object, are passed, and the optical axis of the lens in each pair is disposed closer to the opening that the axis in the light irradiation direction of the corresponding light emitting element.

Preferably, the board includes an opening that receives pieces of light, generated by reflection of the pieces of light from the plurality of light emitting elements in an object, and in the two pairs that are symmetrically disposed in relation to the opening, a symmetrical relationship holds between the relatively positional relationship in one of the pairs and the relatively positional relationship in the other pair.

Preferably, the illumination device further includes seatings that are mounted as many as the light emitting elements while each of the seatings corresponds to one of the plurality of light emitting elements, wherein each of the seatings includes a retaining portion that retains the corresponding lens.

According to one or more embodiments of the present invention, a translucent section of each of the lenses is larger than a light irradiation section of the corresponding light emitting element.

According to one or more embodiments of the present invention, each of the seating is mounted on the board with a relatively positional relationship that is previously determined with respect to the corresponding light emitting element, and the retaining portion retains the lens while the relatively positional relationship of the lens retained by the retaining portion with respect to the seating can be adjusted.

Alternatively, according to one or more embodiments of the present invention, the retaining portion retains the lens with a previously-determined relatively positional relationship of the lens retained by the retaining portion with respect to the seating, and each of the seating is mounted on the board with a relatively positional relationship that is previously determined according to a position on the board on which the corresponding light emitting element is mounted.

Preferably, the lens includes a reflecting surface in at least part of a surface on a side to which the light is incident from the light emitting element.

In accordance with another aspect of the invention, there is provided an illumination device producing method including the steps of: mounting a plurality of light emitting elements on a board such that a light irradiation direction of each light emitting element becomes substantially perpendicular to the board; mounting a plurality of seatings on the board such that each seating corresponds to one of the plurality of light emitting elements; and fixing a plurality of lenses onto the seatings such that each lens corresponds to one of the plurality of seatings, wherein a relatively positional relationship between each lens and the light emitting element corresponding to the lens is determined according to a position on the board in which the light emitting element is disposed.

Preferably, a relatively positional relationship between each lens and the seating corresponding to the lens is determined according to a position on the board on which the seating is mounted in the fixing step.

Preferably, a relatively positional relationship each seating and the light emitting element corresponding to the seating is determined according to a position on the board on which the light emitting element is mounted in the step of mounting the plurality of seatings.

In accordance with one aspect of the invention, in each pair of the light emitting element and the lens, the light is emitted outward from the light emitting element with a non-zero angle defined in each pair with respect to a direction perpendicular to the board defined. Therefore, the illumination device lineup having many variations that respond to various illumination visual fields and work distances can be provided while the cost is controlled. In accordance with another aspect of the invention, the producing method for realizing the illumination device having the many variations can be provided.

BRIEF DESCRIPTION OF THE DRAWINGS

FIGS. 5A and 5B are views for explaining alignment in the illumination unit of the first embodiment;

FIGS. 15A and 15B are views for explaining alignment in the illumination unit of the second embodiment;

FIGS. 19A and 19B are sectional views illustrating a structure of a lens according to a first modification of the embodiments;

FIGS. 22A and 22B are views for explaining an irradiation pattern improvement effect by the lens of the first modification;

DETAILED DESCRIPTION

Figure 1:
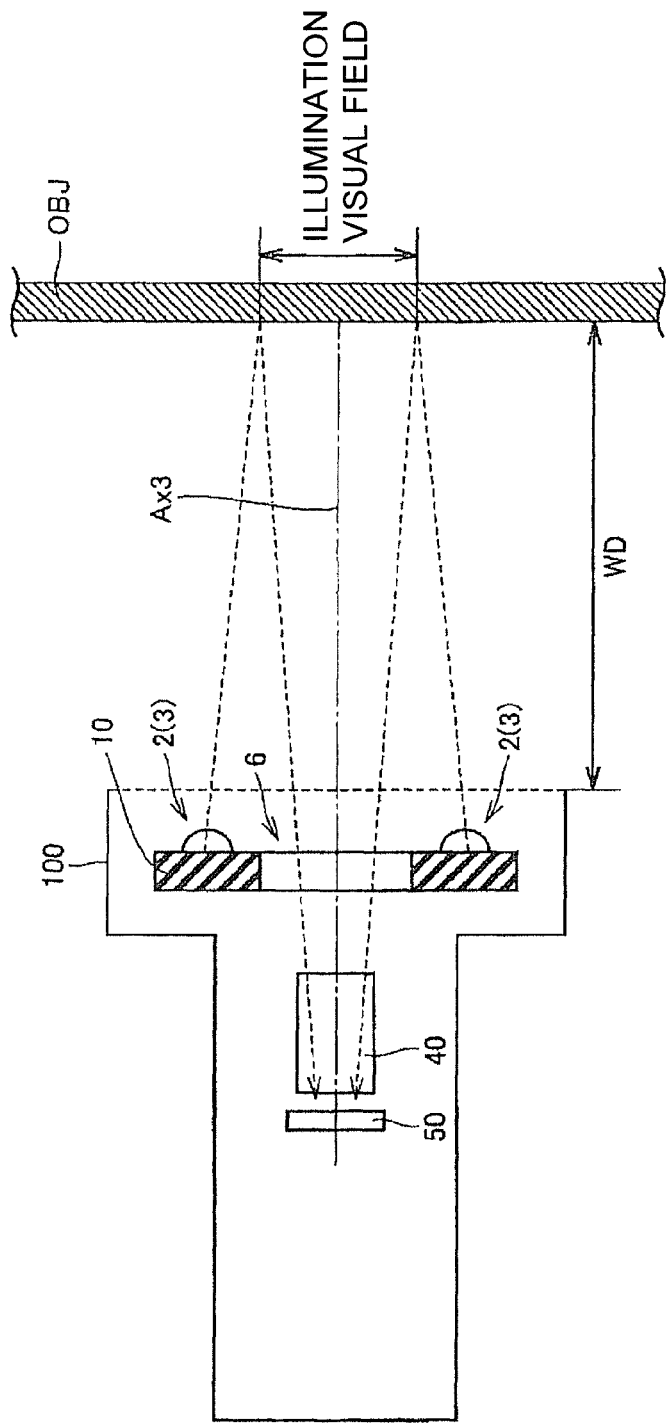
FIG. 1 is a schematic configuration diagram illustrating a main part of a visual sensor according to a first embodiment of the invention.

Hereinafter, embodiments of the present invention will be described with reference to the drawings. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention. In the drawings, an identical or equivalent component is designated by an identical numeral, and the overlapping description is omitted.

[First Embodiment]

In a first embodiment of the invention, an implementation example in which an illumination device is mounted on the visual sensor disclosed in Japanese Unexamined Patent Publication No. 10-320538 is illustrated by way of example.

<A. Entire Device Configuration>

FIG. 1 is a schematic configuration diagram illustrating a main part of a visual sensor according to a first embodiment of the invention. Referring to FIG. 1, the visual sensor of the first embodiment includes an imaging unit 100 that is disposed opposite to a measurement object (hereinafter also simply referred to as "object") OBJ. The imaging unit 100 images a surface (exposed surface) of the object OBJ to obtain image data. The obtained image data is transmitted to a processing unit (not illustrated) to perform image recognition processing. A determination whether the object OBJ is non-defective or defective is made according to the image recognition processing result.

More specifically, the imaging unit 100 includes an illumination unit 10 that emits illumination light, an imaging portion 50 that receives light reflected from the object OBJ illuminated with the illumination light, and a lens unit 40 that is disposed in a preceding step of the imaging portion 50.

The illumination unit 10 includes a board on which plural light emitting elements 25 are mounted, and each light emitting element 25 emits light from the left toward the right in FIG. 1. The light is reflected by a surface of the object OBJ, and the reflected light is incident to the lens unit 40 through an opening 6 provided in the illumination unit 10. The lens unit 40 includes a well-known diaphragm mechanism (not illustrated) or a well-known zoom mechanism (not illustrated) to adjust an amount and a magnification factor of the reflected light incident to the imaging portion 50. That is, optical adjustment is performed such that imaging portion 50 can properly image the object OBJ. Typically the imaging portion 50 is formed by a device such as a CCD (Charge Couple Device) and a CMOS image sensor.

The imaging unit 100 obtains (images) the image data indicating an exposed surface of the object OBJ using the illumination light emitted from the illumination unit 10.

As illustrated in FIG. 1, the "illumination visual field" means a range that can effectively be illuminated by the imaging unit 100, that is, a range that can be irradiated with the intended light amount. In other words, the "illumination visual field" means a size (range) of the object OBJ whose effective image data can be obtained using the imaging unit 100.

As used herein, the "work distance" or "WD" means a distance from the imaging unit 100 to the object OBJ, in which the object OBJ can effectively be irradiated with the illumination light using the imaging unit 100.

<B. Illumination Unit Structure>

Figure 2:
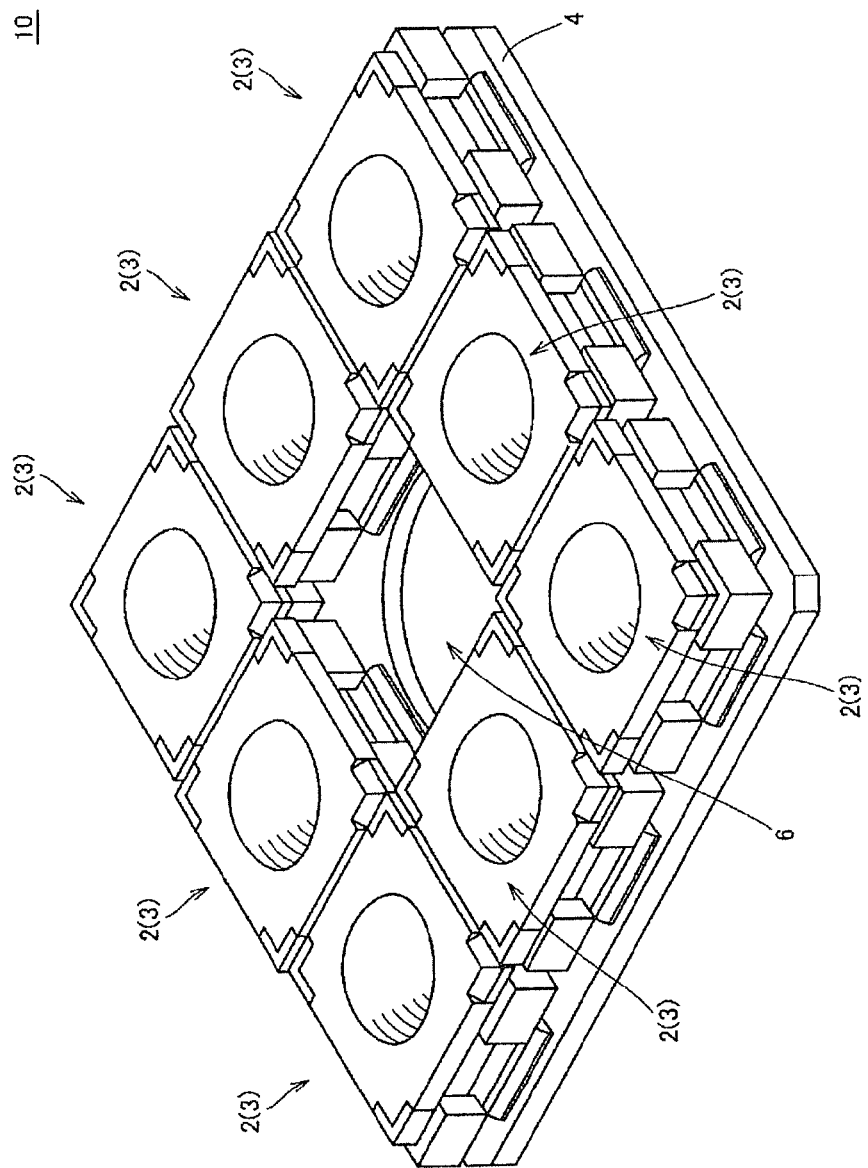
FIG. 2 is a perspective view of an illumination unit of the first embodiment.

FIG. 2 is a perspective view of the illumination unit 10 of the first embodiment. Referring to FIG. 2, the illumination unit 10 of the first embodiment includes a board 4 and plural cells 2 arrayed on the board 4. Each of the cells 2 is a unit that emits the light to illuminate the object OBJ, and the cell 2 includes a pair of light emitting elements and a convex lens as described later. Although FIG. 2 illustrates the configuration in which the eight cells 2 are arrayed, as described later, a configuration in which the number of cells 2 is more than eight or a configuration in which the number of cells 2 is lower than eight can be adopted. In FIG. 2, the cells 2 are arrayed such that the illumination unit becomes a substantially square shape. However, the cells 2 may be arrayed in arbitrary positions according to applications.

The opening 6 is formed in the board 4 such that pieces of light pass through the opening 6. The pieces of illumination light emitted from the plural cells 2 are reflected by the object OBJ to generate the pieces of light. A size of the opening 6 (opening size) is determined according to an opening diameter of the imaging portion 50 illustrated in FIG. 1 and positional relationships of the illumination visual field and WD.

<C. Cell Structure>

Figure 3:
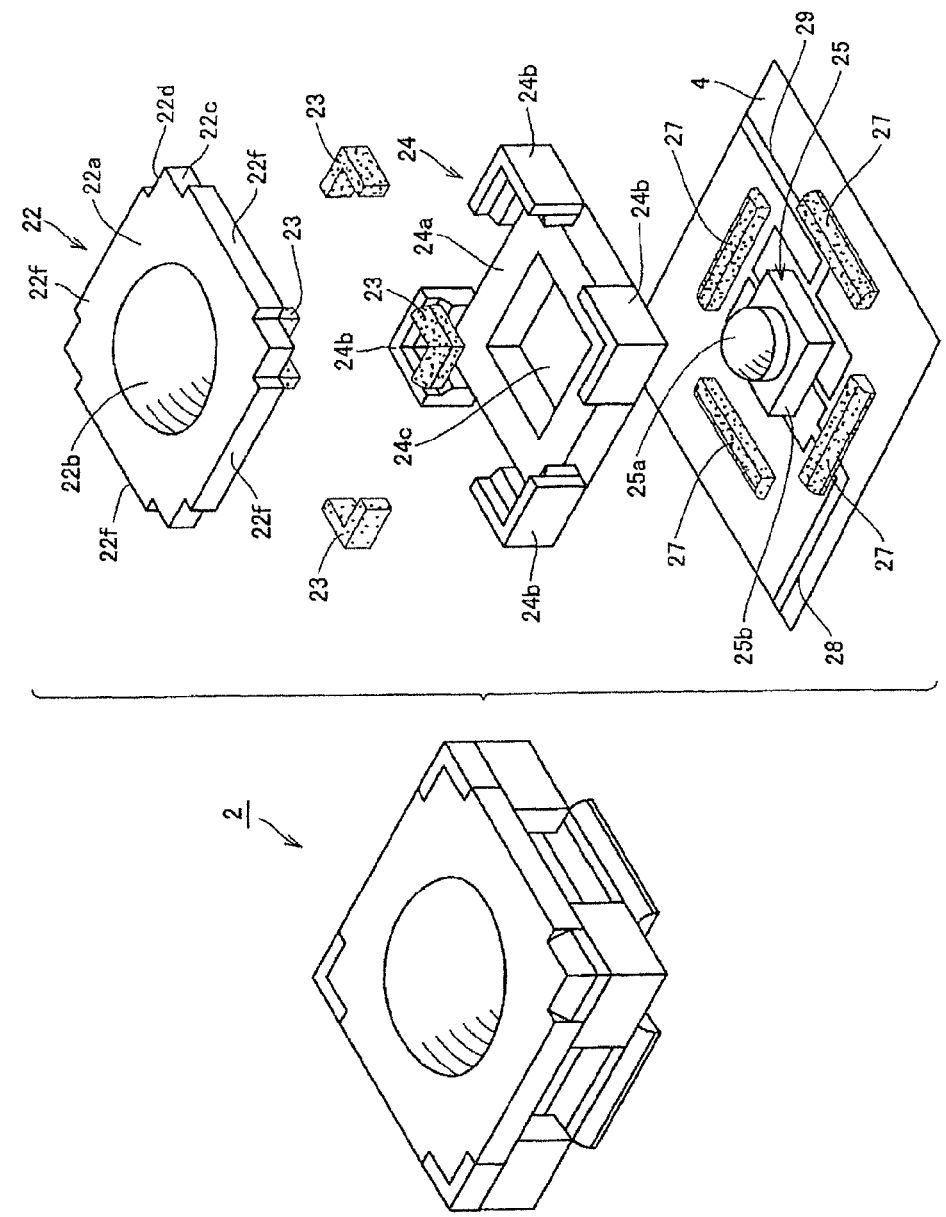
FIG. 3 is an exploded view of a cell constituting the illumination unit of the first embodiment.
Figure 4:
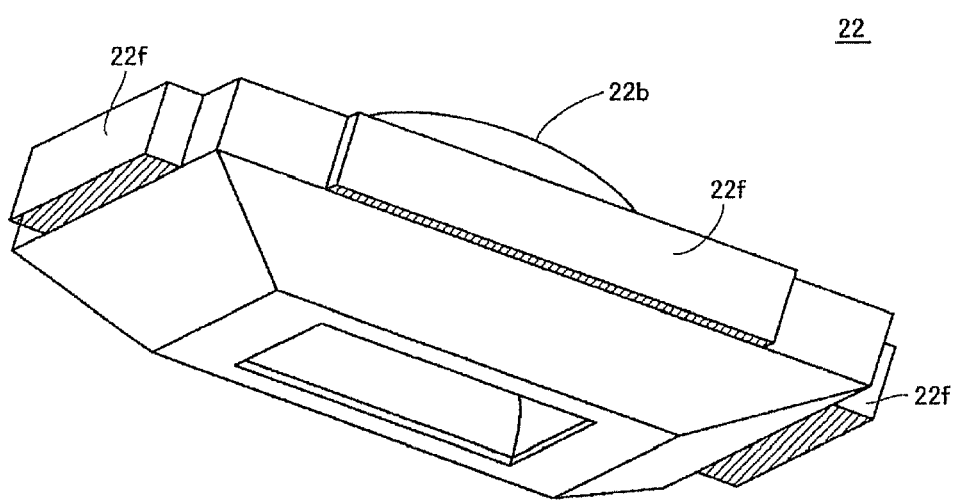
FIG. 4 is a perspective view of a lens of the first embodiment.

FIG. 3 is an exploded view of the cell 2 constituting the illumination unit 10 of the first embodiment. FIG. 4 is a perspective view of the lens of the first embodiment. Referring to FIGS. 3 and 4, the cell 2 includes a lens 22, a seating 24, and a light emitting element 25. The lens 22 and the seating 24 are joined by a bonding agent 23, and the seating 24 and the board 4 are joined by a bonding agent 27.

The light emitting element 25 is a well-known surface mount LED package in which an LED chip is incorporated to form a lens portion 25a and a base portion 25b, and the light emitting element 25 is mounted on the board 4. At this point, because the light emitting element 25 is mounted by a usual surface mounting method without performing such adjustment that the light irradiation direction is oriented toward a specific direction, an optical axis direction of the lens portion 25a, that is, the light irradiation direction of the light emitting element 25 is disposed so as to be substantially perpendicular to the surface of the board 4. Typically, pads 28 and 29 formed in the board 4 are electrically connected and mechanically fixed to electrodes (not illustrated) formed in the base portion 25b of the light emitting element 25.

The seating 24 includes a bottom portion 24a having a square frame shape, and the seating 24 is disposed so as to surround the light emitting element 25 mounted on the board 4. At this point, the seatings 24 are mounted on the board 4 as many as the light emitting elements 25 mounted on the board 4. Each seating 24 corresponds to one of the light emitting elements 25 mounted on the board 4. The bonding agent 27 is applied in a proper portion on the board 4 to fix the seating 24. In the first embodiment, the seating 24 is mounted on the board 4 while having a predetermined relatively positional relationship with respect to the corresponding light emitting element 25. Typically, the seating 24 is mounted on the board 4 such that a center axis of an opening 24c of the seating 24 is aligned with a center axis of the light emitting element 25. A size (area) of the opening 24c of the seating 24 is larger than a sectional area of the light emitting element 25.

A retaining portion 24b is formed in the seating 24 in order to retain the corresponding lens 22. The lens 22 is mounted on the upper surface of the retaining portion 24b, which allows the lens 22 to be retained above the bottom portion 24a by a predetermined distance.

The lens 22 is positioned in the seating 24 and the lens 22 outputs the illumination light generated in the light emitting element 25 to the outside. That is, the lenses 22 are disposed as many as the light emitting elements 25 mounted on the board 4, and each lens 22 is paired with one of the light emitting elements 25. In the lens 22, a base portion 22a and a translucent convex lens portion 22b are integrally formed. The incoming light mainly from light emitting element 25 converges through the convex lens portion 22b. Although both the base portion 22a and the convex lens portion 22b may have the translucency, the light from the light emitting element 25 is positioned so as to be mainly transmitted through the convex lens portion 22b.

As described later, in the cell 2 of the first embodiment, the illumination unit 10 having the desired illumination visual field and WD is provided by properly setting the relatively positional relationship between the lens 22 and the light emitting element 25. That is, in each cell 2, the lens 22 and the corresponding light emitting element 25 are disposed with the relatively positional relationship in which the light from the light emitting element 25 is output with a non-zero angle determined in each cell with respect to the direction perpendicular to the board 4.

Therefore, the retaining portion 24b of the seating 24 retains the lens 22 such that the relatively positional relationship between the lens 22 and the seating 24 can be adjusted.

Specifically, an upper surface of the retaining portion 24b is formed into an L-shaped flat surface. On the other hand, a pair of notches 22c and 22d is formed in each of four corners of the base portion 22a of the lens 22, and a lower surface of an end portion 22f except the notches of the base portion 22a is formed into a rectangular flat surface. The lens 22 and the seating 24 are fixed to the notches 22c and 22d by the bonding agent 23 while the lower surface of the end portion 22f is placed on the upper surface of the retaining portion 24b.

That is, as illustrated in FIG. 4, the lens 22 is retained such that the whole or part of the lower surface (hatched portion) of the end portion 22f of the lens 22 is in contact with the upper surface of the retaining portion 24b.

The shapes and sizes of the seating 24 and lens 22 are designed with the above-described relationship, which allows the lens 22 to be positioned with respect to the seating 24 such that the desired relatively positional relationship is obtained.

As described above, a section in the convex lens portion 22b of the lens 22, that is, a translucent section of the lens 22 is larger than a section in the lens portion 25a of the corresponding light emitting element 25, that is, a light emitting section of the light emitting element 25 such that the lens 22 can be disposed while deviated (biased) from the center axis of the light emitting element 25 by a predetermined distance. The sectional size of the convex lens portion 22b is designed in consideration of a clearance between the seating 24 and the lens 22.

<D. Adjustment by Alignment>

Figure 6:
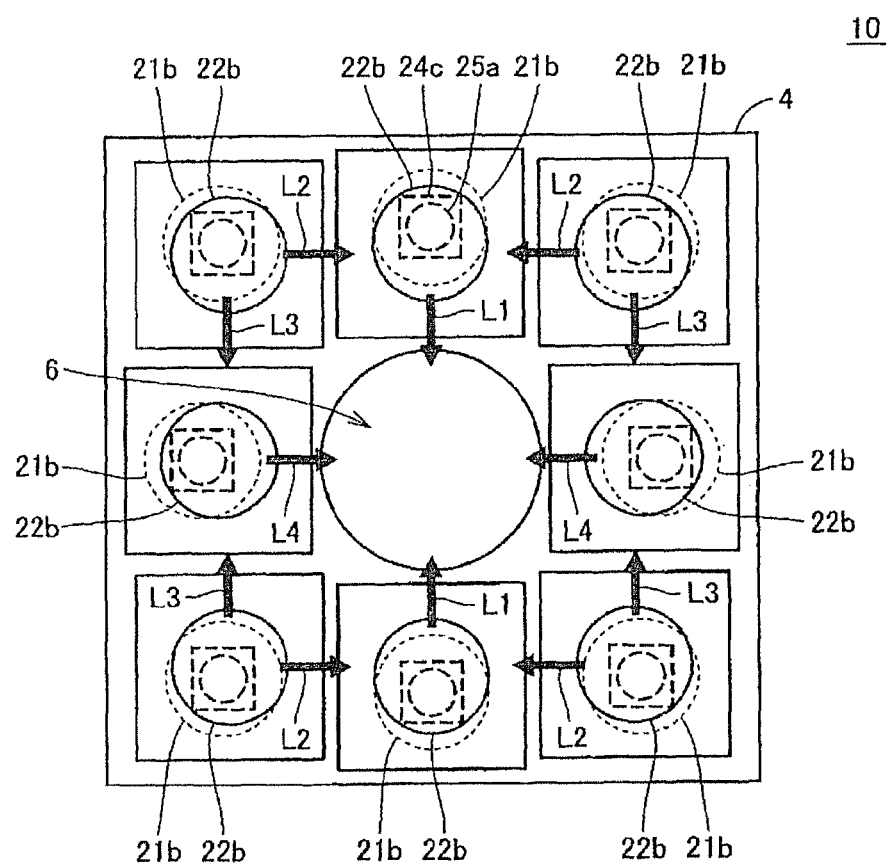
FIG. 6 illustrates a state of the alignment in the illumination unit of the first embodiment.
Figure 7:
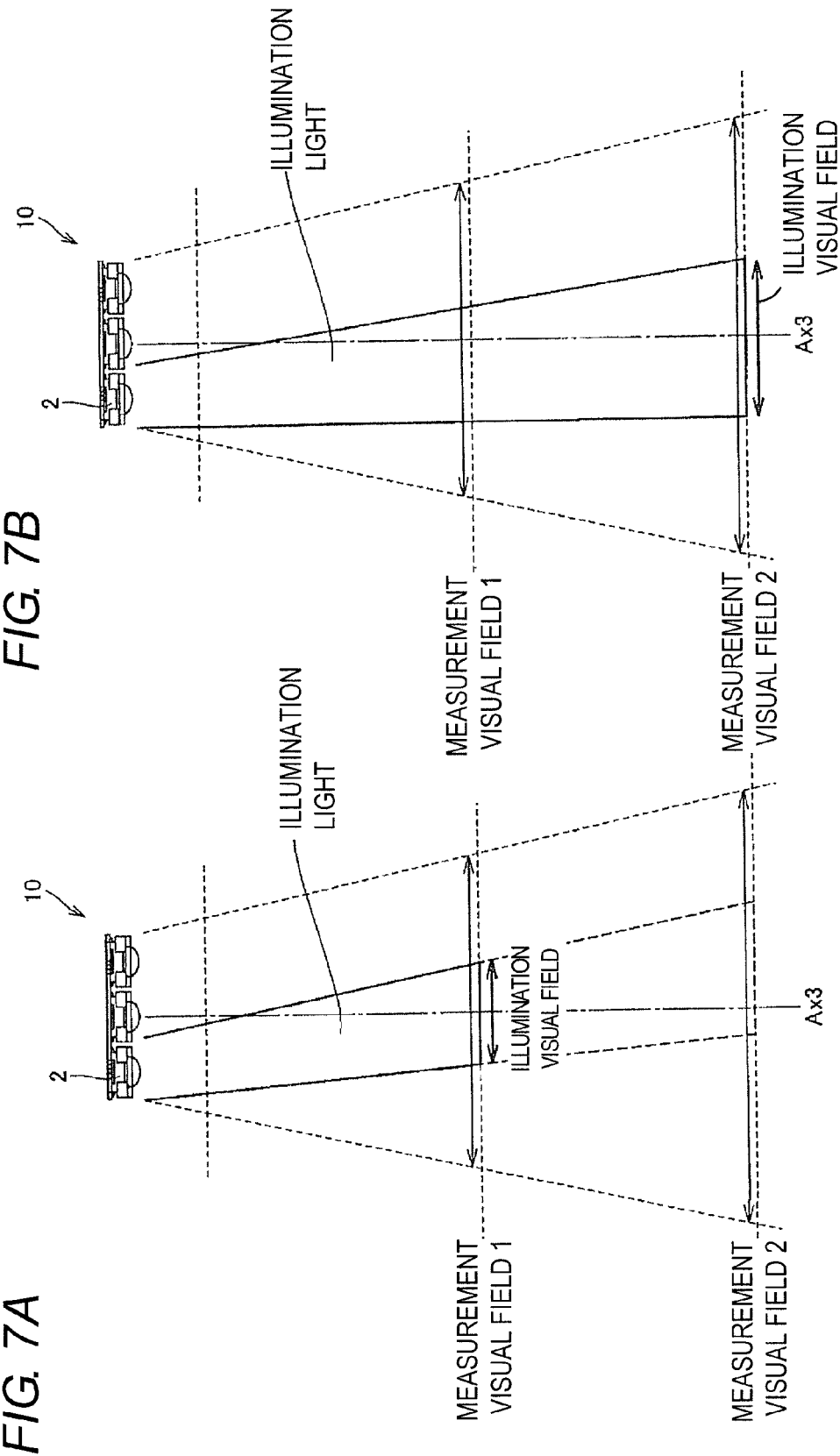
FIGS. 7A and 7B are views for explaining a method for providing a variation of a work distance in the illumination unit of the first embodiment.

FIG. 5 is a view for explaining alignment in the illumination unit 10 of the first embodiment. FIG. 6 illustrates a state of the alignment in the illumination unit 10 of the first embodiment. FIG. 7 is a view for explaining a method for providing a variation of the work distance in the illumination unit 10 of the first embodiment.

FIG. 5A illustrates a state in which the lens 22 is positioned such that an optical axis Ax1 in a light irradiation direction of the light emitting element 25 is aligned with an optical axis Ax2 of the center of the lens 22. FIG. 5B illustrates a state in which the lens 22 is disposed while deviated to the right by a predetermined distance with respect to the state illustrated in FIG. 5A. Hereinafter a manipulation to adjust the relatively positional relationship and the adjusted state are also referred to as "alignment". As described above, the relatively positional relationship between the light emitting element 25 and the seating 24 is previously determined in the cell 2 of the first embodiment, and the relatively positional relationship of the lens 22 with respect to the seating 24 is adjusted (lens alignment) to provide the variations of the WDs and the illumination visual fields of the illumination light output from the illumination unit 10.

More specifically, as illustrated in FIG. 5A, when the optical axis Ax1 of the light emitting element 25 is aligned with the optical axis Ax2 of the lens 22, illumination light B1 generated by the light emitting element 25 propagates along optical axis Ax1. At this point, because the optical axis Ax2 of the lens 22 exists on the same straight line as the optical axis Ax1, the illumination light B1 passing through the lens 22 is output as illumination light B2 while a propagation direction of the illumination light B1 is retained.

On the other hand, as illustrated in FIG. 5B, when the optical axis Ax2 of the lens 22 is deviated from the optical axis Ax1 of the light emitting element 25, the propagation direction of the illumination light B1 is changed after the illumination light B1 generated by the light emitting element 25 is incident to the lens 22. Because the illumination light B1 incident to the lens 22 converges toward the center axis of the lens 22, the resultant illumination light B2 is output in the direction in which the illumination light B2 is inclined with respect to the optical axis Ax1 of the light emitting element 25 by a predetermined angle of non-zero. Because the optical axes Ax1 and Ax2 are perpendicular to the board 4, the illumination light B2 output to the outside from the illumination unit 10 propagates with the non-zero angle that is determined in each cell with respect to the direction perpendicular to the board 4.

As illustrated in FIG. 5, the propagation direction of the illumination light B2 output from the illumination unit 10 is inclined to the same direction as the alignment direction of the lens 22. That is, in each cell 2, the lens 22 is disposed while deviated to the direction in which the light from the light emitting element 25 should be output with respect to the state in which the lens 22 is positioned to the optical axis Ax1 in the light irradiation direction of the corresponding light emitting element 25.

The output direction of the illumination light B2 is largely inclined with respect to the optical axis Ax1 with increasing alignment amount (displacement amount) of the lens 22.

The desired illumination visual field and WD can be realized by performing the alignment of the lens 22 in the proper displacement direction and with the proper displacement amount. In other words, various alignment directions and alignment amounts are set while the same light emitting element 25 and lens 22 are used, which allows the illumination unit 10 having various illumination visual fields and WDs to be provided. Accordingly, it is not necessary that the light emitting elements 25 and the lenses 22 be individually designed as many as the variations of the illumination visual fields and WDs, or it is not necessary to obliquely mount the light emitting element, which allows the production cost to be reduced.

Each cell 2 is aligned according to the position of the cell 2 on the board 4 such that the pieces of illumination light output from the cells 2 included in the illumination unit 10 become the intended illumination visual field and WD as a whole. For example, as illustrated in FIG. 6, when the illumination light is output toward the center axis (corresponding to the center of the opening 6) of the illumination unit 10, the lens 22 in each cell 2 is disposed in a position deviated to the direction closer to the opening 6 with respect to the light emitting element 25.

In FIG. 6, the position of the convex lens portion 22b is illustrated by a broken line (numeral 21b) in the state (corresponding to the state of FIG. 5A) in which the optical axis Ax1 of the light emitting element 25 is aligned with the optical axis Ax2 of the convex lens portion 22b. As described above, because the section in the convex lens portion 22b of the lens 22 is configured to become larger than the section in the lens portion 25a of the corresponding light emitting element 25, the lens portion 25a falls within the region of the numeral 21b when viewed from the direction perpendicular to the surface of the board 4 as illustrated in FIG. 6. The lens 22 of the cell 2 located in the center of the uppermost stage in FIG. 6 is deviated from the reference state illustrated by the numeral 21b so as to be close to the opening 6 (an alignment amount L1 in a downward direction in FIG. 6). Similarly, in the cell 2 located on the left of the uppermost stage in FIG. 6, the lens 22 is deviated so as to be close to the opening 6 (an alignment amount L2 in a rightward direction and an alignment amount L3 in the downward direction in FIG. 6). In the cell 2 located on the left in the middle stage in FIG. 6, the lens 22 is deviated so as to be close to the opening 6 (an alignment amount L4 in the rightward direction in FIG. 6).

Other cells 2 are aligned according to the similar rule. Each of the cells 2 constituting the illumination unit 10 is aligned with the displacement direction and with the displacement amount according to the position of each cell 2 on the board 4 such that the desired illumination visual field and WD can be realized.

FIG. 6 illustrates the alignment example when the illumination light is output in the center direction of the illumination unit 10. When the illumination light is output in another direction, the alignment is performed according to the desired irradiation direction.

As described above, the relatively positional relationship between the light emitting element 25 and the lens 22 in each cell 2 is determined according to the position on the board 4 in which the corresponding light emitting element 25 is disposed. In each cell 2, the lens 22 is disposed such that the optical axis Ax2 (see FIG. 5) of the lens 22 is brought closer to the opening 6 than the optical axis Ax1 (see FIG. 5) in the light irradiation direction of the corresponding light emitting element.

As illustrated in FIG. 6, in the configuration in which the plural cells 2 are symmetrically disposed in relation to the opening 6, in the two cells 2 symmetrically disposed in relation to the opening 6, a symmetrical relationship holds between the relatively positional relationship in one of the cells 2 and the relatively positional relationship in the other cell 2. For example, the alignment amount (the alignment amount L1 in the downward direction in FIG. 6) in the cell 2 located in the center of the uppermost stage illustrated in FIG. 6 is equalized to the alignment amount (the alignment amount L1 in the upward direction in FIG. 6) in the cell 2 located in the center of the lowermost stage illustrated in FIG. 6.

A relationship between the alignment and the adjustment of the illumination visual field and work distance (WD) will be described below. FIG. 7A illustrates an irradiation state in which the alignment amount in the cell 2 is relatively large, and FIG. 7B illustrates an irradiation state in which the alignment amount in the cell 2 is relatively small. In the cell 2, it is assumed that the lens 22 is aligned in the direction of the opening 6 of the illumination unit 10.

It is also assumed that the lens unit 40 and the imaging portion 50 are aligned on a predetermined axis (see FIG. 1). Therefore, a range where the imaging portion 50 can image the object OBJ (hereinafter referred to as "measurement visual field") becomes a range centered on an optical axis Ax3 of the imaging portion 50. Preferably the optical axis Ax3 is set so as to penetrate through the center of the opening 6 of the illumination unit 10.

In the example illustrated in FIG. 7A, because of the relatively large alignment amount, the illumination light from the cell 2 on the left in FIG. 7A is output with a relatively large inclination (outgoing angle) with respect to the direction perpendicular to the board of the illumination unit 10. Therefore, the range centered on the optical axis Ax3 is irradiated in the position relatively close to the illumination unit 10 (the position corresponding to the measurement visual field 1 illustrated in FIG. 7A). On the other hand, the range deviated from the measurement visual field of the imaging portion 50 is irradiated in the position farther away from the illumination unit 10 (the measurement visual field 2 illustrated in FIG. 7A).

In principle, according to one or more embodiments of the present invention, illumination intensity within the measurement range of the imaging portion 50 is even. Therefore, in the example illustrated in FIG. 7A, the WD of the illumination unit 10 becomes the position corresponding to the measurement visual field 1, and the range irradiated in the measurement visual field 1 becomes the illumination visual field. In other words, the WD of the illumination unit 10 means a place where the center of the illumination visual field is aligned with the optical axis Ax3 that is of the center of the measurement visual field of the imaging portion 50. On the other hand, in the measurement visual field 2, because an in-plane light amount distribution becomes uneven, the object OBJ cannot properly be imaged. In one or more embodiments of the invention, the work distance (WD) does not mean a specific value, but a distance range having a certain degree of width where the measurement visual field of the imaging portion 50 can properly be illuminated.

In the example illustrated in FIG. 7B, the alignment amount is set such that the center of the illumination visual field irradiated with the light from the illumination unit 10 is aligned with the optical axis Ax3 in the position of the measurement visual field 2. That is, the outgoing angle of the illumination light is decreased such that the object OBJ located farther away from the illumination unit 10 can properly be irradiated with the illumination light. In the example illustrated in FIG. 7B, contrary to the example illustrated in FIG. 7A, the object OBJ cannot properly be imaged because the in-plane light amount distribution becomes uneven in the measurement visual field 1.

The alignment amount is appropriately be adjusted in each cell 2 at the production stage, which allows the illumination unit 10 having the proper work distance (WD) to be provided according to a distance of the object OBJ imaged by the imaging portion 50.

Extensive lineups such as a product having the measurement visual field of 5 to 10 mm and the WD of 35 to 50 mm and a product having the measurement visual field of 10 to 50 mm and the WD of 35 to 200 cm can be provided while the common lens 22, seating 24, and light emitting element 25 are used.

(Design Example)

A typical design example will be described below.

Figure 8:
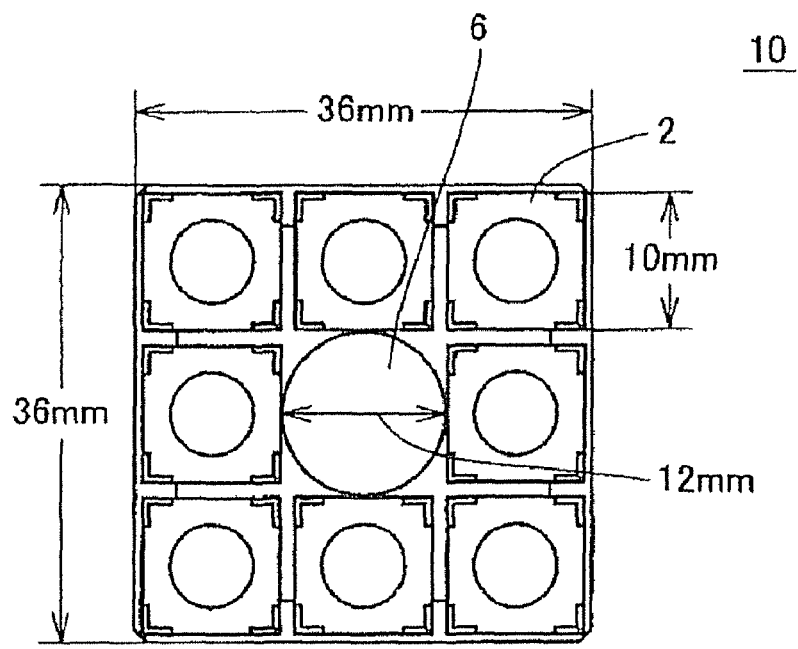
FIG. 8 illustrates a size of an implementation example of the illumination unit of the first embodiment.

FIG. 8 illustrates a size of the implementation example of the illumination unit 10 of the first embodiment. As illustrated in FIG. 8, it is assumed that the illumination unit 10 has the board size of 36 mm×36 mm, it is assumed that each cell 2 (an outer shape of the seating 24) has the size of 10 mm×10 mm, and it is assumed that opening 6 has the diameter of 12 mm.

At this point, the following cases are considered:

(1) the measurement visual field ranges from 5 to 10 mm (diameter value) and the work distance (WD) ranges from 35 to 40 mm, and (2) the measurement visual field ranges from 10 to 50 mm (diameter value) and the work distance (WD) ranges from 35 to 200 mm.

The case (1) corresponds to the positional relationship illustrated in FIG. 7A, and the case (2) corresponds to the positional relationship illustrated in FIG. 7B.

According to a computer simulation, specifications expressed in the case (1) can be realized with the alignment amount of 0.4 mm by deviating the relatively positional relationship between the lens 22 and the light emitting element 25. Specifications expressed in the case (2) can be realized with the alignment amount of 0.2 mm by deviating the relatively positional relationship between the lens 22 and the light emitting element 25.

<E. Adjustment by Lens Shape>

As described above, the variations of the illumination visual fields and work distances (WD) can be provided by adjusting (alignment) the relatively positional relationship between the light emitting element 25 and the lens 22. Alternatively, more variations of the illumination visual fields and work distances (WD) can be provided by preparing plural kinds of lenses 22 with different shapes.

Figure 9:
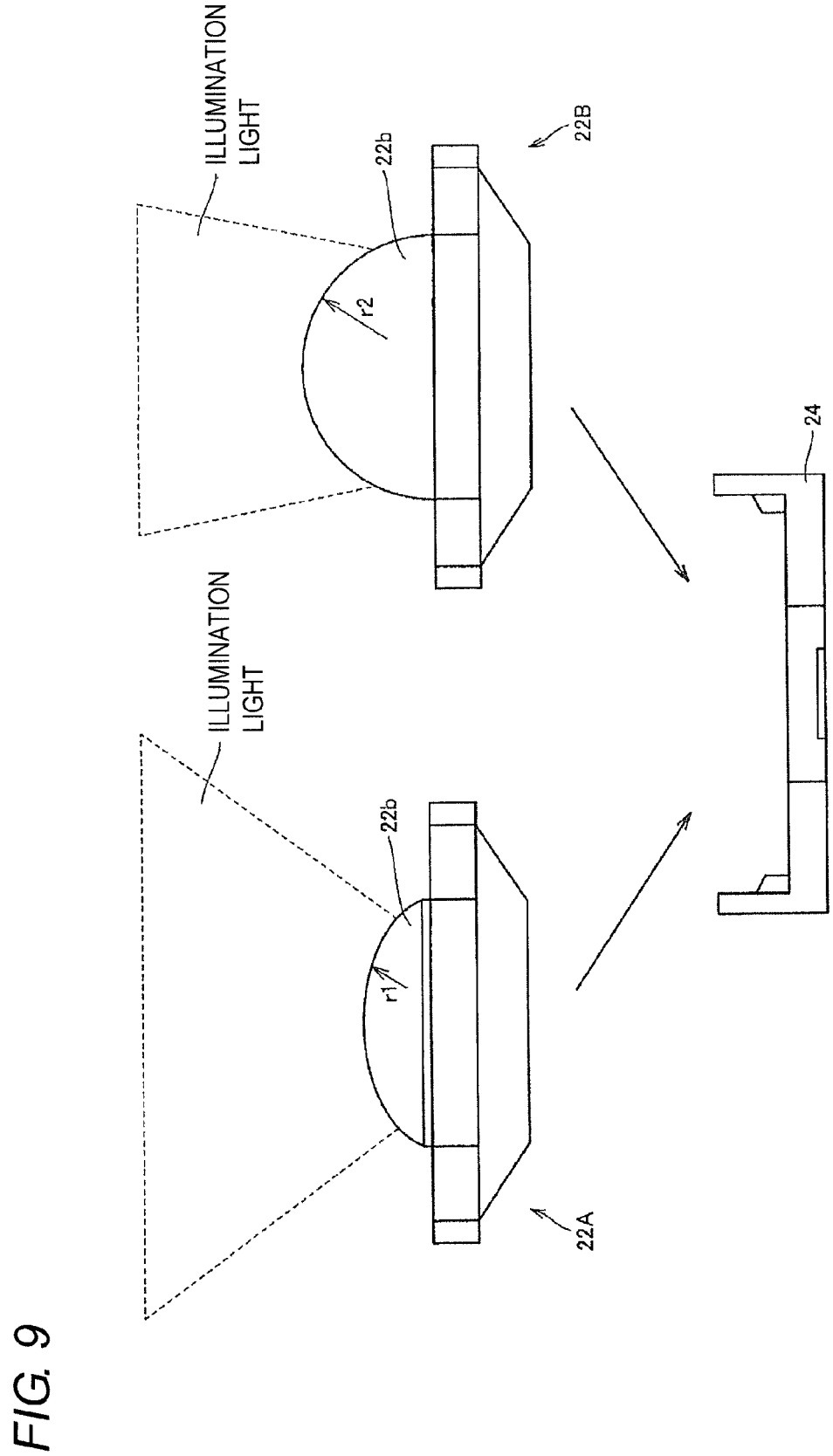
FIG. 9 illustrates adjustment of an irradiation direction by different lens shapes in the illumination unit of the first embodiment.
Figure 10:
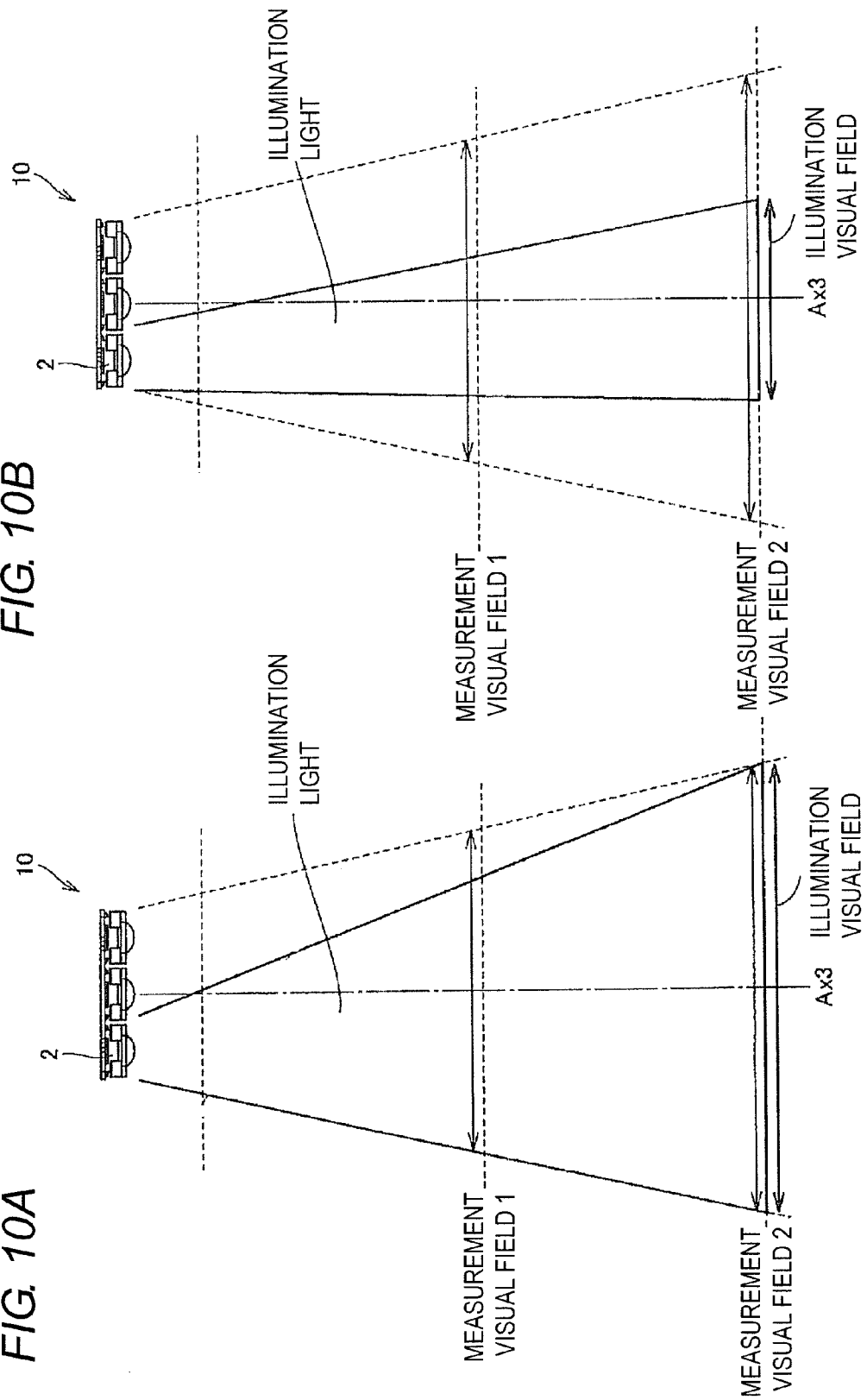
FIGS. 10A and 10B are views for explaining a method for providing the variation of the work distance in the illumination unit of the first embodiment.

FIG. 9 illustrates adjustment of an irradiation direction by different lens shapes in the illumination unit 10 of the first embodiment. FIG. 10 is a view for explaining a method for providing the variation of the work distance in the illumination unit 10 of the first embodiment.

Referring to FIG. 9, a difference of an optical behavior using two kinds of lenses 22A and 22B having different lens diameters will be described as an typical example of the plural kinds of lenses 22 having different shapes. FIG. 9A illustrates an example in which the lens 22A having a relatively large curvature radius r1 is used, FIG. 9B illustrates an example in which having a relatively small curvature radius r2 (r2<r1) is used.

As illustrated in FIG. 9A, in the lens 22A having the relatively large curvature radius r1, because a refractive index to the illumination light propagating through the lens 22A becomes small, a radius of convergence is relatively increased. Therefore, a light flux diameter of the illumination light output through the lens 22A is relatively large, and the wider range is irradiated. That is, the illumination visual field of each cell 2 is relatively increased.

On the other hand, as illustrated in FIG. 9B, in the lens 22B having the relatively small curvature radius r2, because a refractive index to the illumination light propagating through the lens 22B becomes large, a radius of convergence is relatively decreased. Therefore, a light flux diameter of the illumination light output through the lens 22B is relatively small, and the narrower range is irradiated. That is, the illumination visual field of each cell 2 is relatively decreased.

FIG. 10 illustrates the illumination visual fields when the lenses having the different lens diameters are used as illustrated in FIG. 9. FIG. 10A illustrates the case in which the lens 22A has the relatively large curvature radius as illustrated in FIG. 9A. In such cases, the illumination visual field can be provided so as to cover the whole of the measurement visual field 2 even if the measurement visual field 2 is located far away from the illumination unit 10. On the other hand, FIG. 10B illustrates the case in which the lens 22B has the relatively small curvature radius as illustrated in FIG. 9B. In such cases, the illumination visual field of one cell 2 cannot cover the whole of the measurement visual field 2.

However, when the amounts of pieces of illumination light output from the cells 2 are equal to one another, the illumination intensity in the illumination visual field of FIG. 10A becomes smaller than that of the illumination visual field of FIG. 10B. Therefore, the range irradiated with the illumination light from each cell 2 is appropriately designed in consideration of the number of cells 2 constituting the illumination unit 10, the disposition configuration of the cells 2, and the position and area of the measured object OBJ.

The illumination visual field can easily be changed by preparing the plural kinds of lenses 22 having different curvature radiuses (refractive indexes), and therefore a product group having more variations can be provided while the cost is controlled.

<F. Producing Process>

Figure 11:
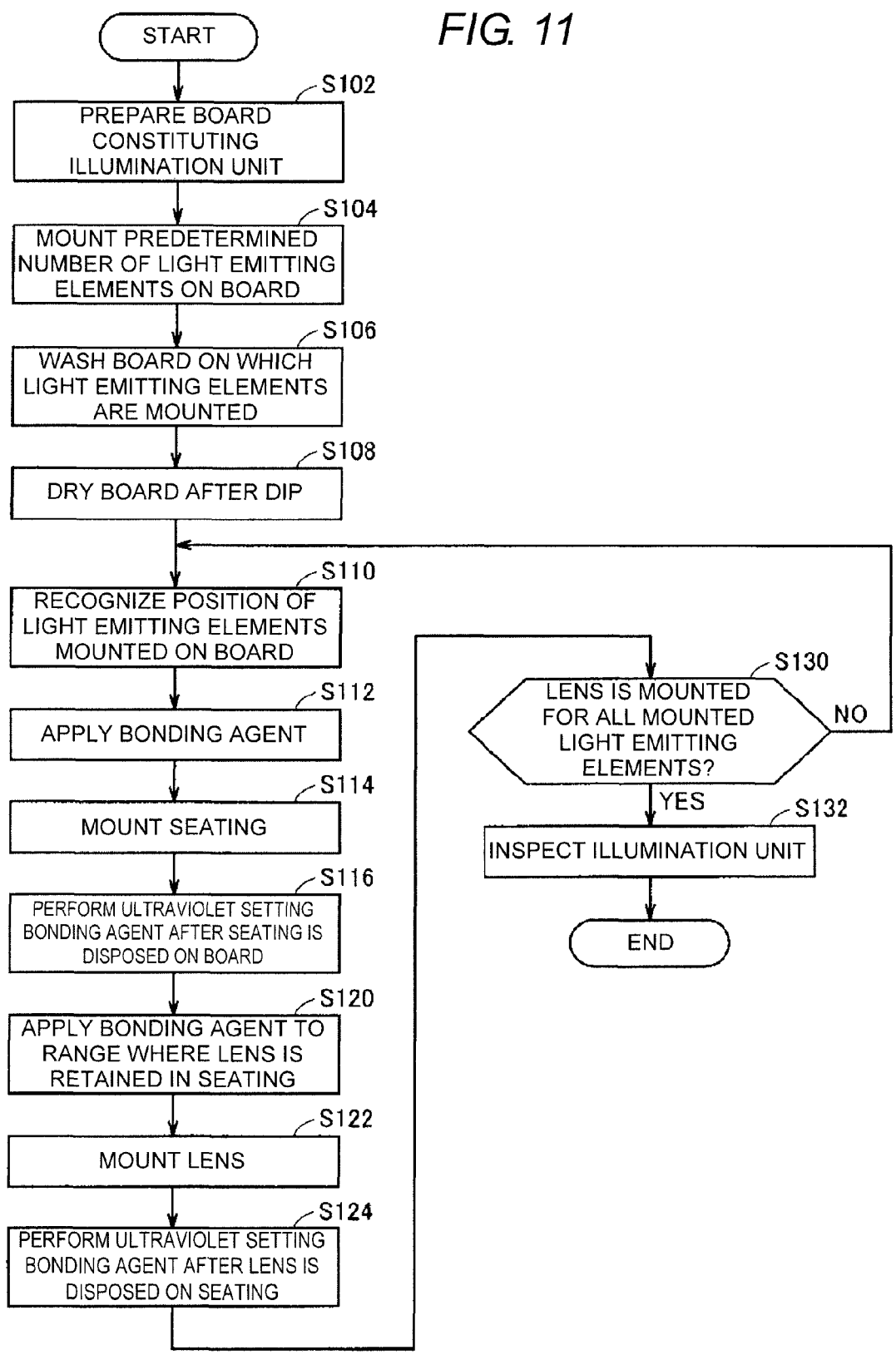
FIG. 11 is a flowchart illustrating a process of producing the illumination unit of the first embodiment.
Figure 12:
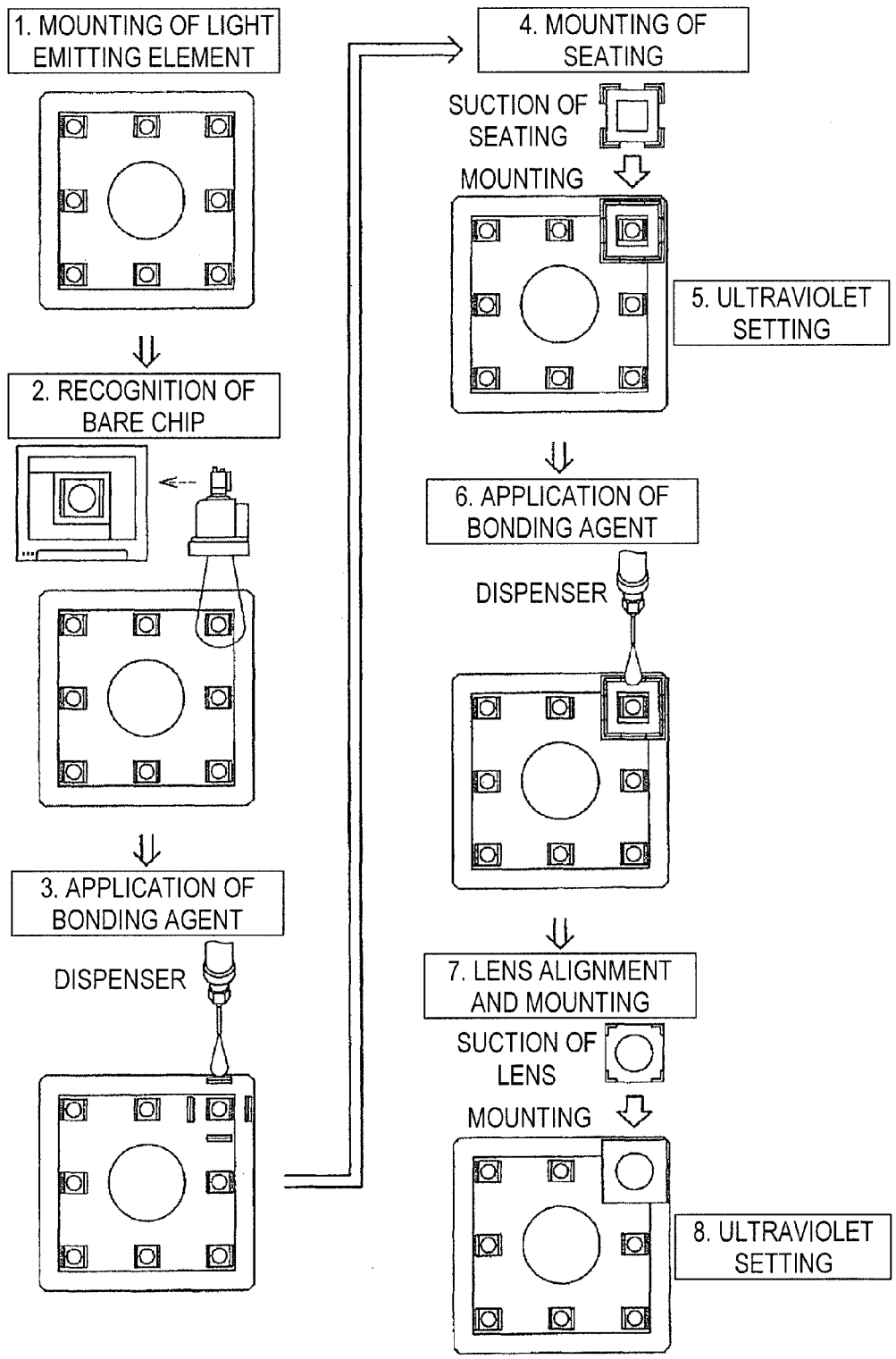
FIG. 12 is a schematic diagram illustrating the process of producing the illumination unit of the first embodiment.

FIG. 11 is a flowchart illustrating a process of producing the illumination unit 10 of the first embodiment. FIG. 12 is a schematic diagram illustrating the process of producing the illumination unit 10 of the first embodiment. FIG. 13 is a view for explaining each state during the production of the illumination unit 10 of the first embodiment.

Referring to FIG. 11, in Step S102, the board 4 constituting the illumination unit 10 is prepared. In Step S104, the predetermined light emitting elements 25 are mounted on the prepared board 4. Typically, the light emitting elements 25 are collectively or sequentially mounted in predetermined positions on the prepared board 4 by a well-known surface mounting method. That is, after cream solder is printed on the pads 28 and 29, the light emitting element 25 is placed with a chip mounter, the cream solder is melted by heating the cream solder in a reflow furnace, the electrode (not illustrated) of the light emitting element 25 is soldered to the pad to fix the light emitting element 25 to the board 4. Therefore, the plural light emitting elements 25 are mounted on the board 4 such that the light irradiation direction of each light emitting element 25 is substantially perpendicular to the board 4. When the general surface mounting method is adopted, the position in which each light emitting element 25 is mounted on the board 4 is deviated within a predetermined range.

Figure 13A:
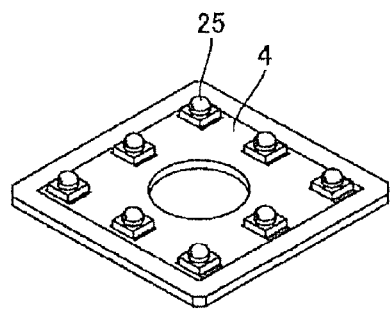
FIGS. 13A to 13E are views for explaining each state during the production of the illumination unit of the first embodiment.

In Step S106, the board 4 on which the light emitting elements 25 are mounted is washed (typically, a dipping treatment in an isopropyl alcohol solution). In Step S108, the board 4 is dried in a constant-temperature oven after the dip. The board 4 illustrated in a process of "1. mounting of light emitting element" of FIG. 12 is obtained after Step S108 is performed. FIG. 13A illustrates the board 4 in the state in which the eight light emitting elements 25 are mounted.

When the board 4 in the state in which the eight light emitting elements 25 are mounted is obtained through the process, the flow goes to a process of mounting the seatings 24 from Step S110.

In Step S110, the positions in which the light emitting elements 25 are mounted on the board 4 are recognized. This is because, as described above, the light emitting element 25 mounted on the board 4 is not always mounted on the board 4 with the same positional relationship. More specifically, as illustrated in a process of "2. recognition of bare chip" of FIG. 12, the position of the bare chip (the light emitting element 25 in the state in which an exterior package and the like are not attached to the light emitting element 25) is specified using the well-known image processing technique.

Figure 13B:
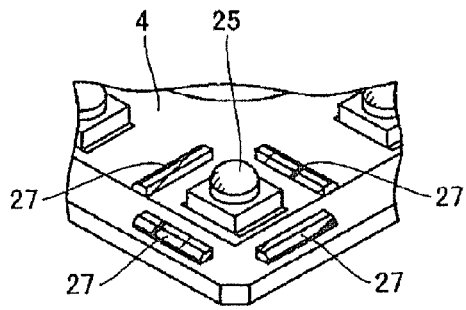

In Step S112, the bonding agent 27 is applied in the range that is determined according to the position of the light emitting element 25 specified on the board 4. In the working process in Step S112, an ultraviolet setting resin (hereinafter also referred to as "UV bonding agent") is frequently used as the bonding agent 27. Alternatively, a thermosetting bonding agent or a visible light curing bonding agent may be used as the bonding agent 27. At this point, as illustrated in a process of "3. application of bonding agent" of FIG. 12, the predetermined amount of bonding agent 27 is applied after a well-known dispenser (an apparatus that quantitatively ejects a liquid) is positioned according to the image recognition result. FIG. 13B illustrates the board 4 in the state in which the bonding agent 27 is applied to four sides surrounding the light emitting element 25.

In Step S114, the seating 24 is mounted on the target light emitting element 25 so as to have the predetermined relatively positional relationship. In the first embodiment, the seating 24 is mounted such that the center of the opening 24c of the seating 24 is matched with the center of the light emitting element 25. More specifically, as illustrated in a process of "4. mounting of seating" of FIG. 12, the seating 24 is positioned in the intended relative position while sucked with a well-known robot apparatus.

Figure 13C:
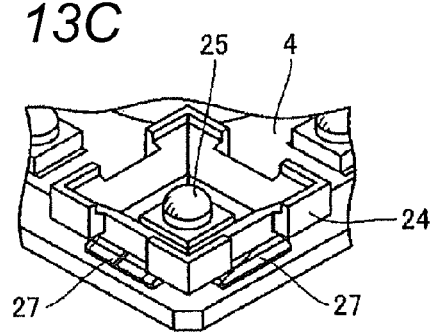

In Step S116, the ultraviolet curing of the bonding agent 27 is performed when the seating 24 is disposed in the board 4. More specifically, as illustrated in a process of "5. UV curing" of FIG. 12, the bonding agent 27 is irradiated with a predetermined amount of ultraviolet ray using a well-known ultraviolet irradiation apparatus. FIG. 13C illustrates the state in which the seating 24 is mounted so as to surround the light emitting element 25.

In the process between Steps S114 and S116, a pre-annealing treatment (heat treatment) may be performed in order to stabilize the seating 24 and the bonding agent 27.

The mounting of the seating 24 is completed in one cell 2 through the processes in Steps S110 and S116. That is, in the processes in Steps S110 to S116, each of the plural seatings 24 is mounted on the board 4 so as to become the predetermined relatively positional relationship with one of the plural light emitting elements 25.

Then the alignment and mounting of the lens 22 are performed. In Step S120, the bonding agent 23 is applied to the range where the lens 22 is retained in the seating 24. Similarly to the bonding agent 27, the ultraviolet setting resin (hereinafter also referred to as "UV bonding agent") is frequently used as the bonding agent 23. Alternatively, the thermosetting bonding agent or the visible light curing bonding agent may be used as the bonding agent 23. At this point, as illustrated in a process of "6. application of bonding agent" of FIG. 12, the predetermined amount of bonding agent 23 is applied to the four corners of the retaining portion 24b of the seating 24.

In Step S122, the lens 22 is mounted on the seating 24 so as to have the desired relatively positional relationship according to the position. That is, as illustrated in FIG. 6, the lens 22 is positioned based on the corresponding seating 24 such that the alignment amount is generated according to the position on the board 4. More specifically, as illustrated in a process of "7. lens alignment and mounting" of FIG. 12, the lens 22 is positioned in the intended relative position while sucked with the well-known robot apparatus.

Figure 13D:
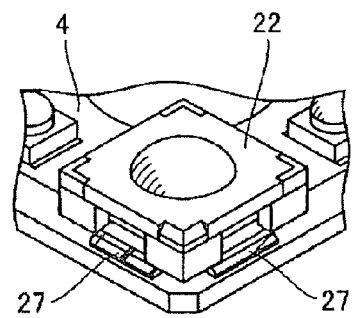

In Step S124, the ultraviolet curing of the bonding agent 23 is performed when the lens 22 is disposed in the seating 24. More specifically, as illustrated in a process of "8. UV curing" of FIG. 12, the bonding agent 23 is irradiated with the predetermined amount of ultraviolet ray using the well-known ultraviolet irradiation apparatus. FIG. 13D illustrates the state in which the lens 22 is mounted on the seating 24.

In the process between Steps S122 and S124, the pre-annealing treatment (heat treatment) may be performed in order to stabilize the lens 22 and the bonding agent 23.

The mounting of the lens 22 is completed in one cell 2 through the processes in Steps S120 and S124. That is, in the processes in Steps S120 to S124, each of the plural lenses 22 is fixed onto the seating 24 so as to correspond to one of the plural seatings 24. The relatively positional relationship between each lens 22 and the corresponding light emitting element 25 is determined such that the light is emitted outward from the light emitting element 25 corresponding to each lens 22 with a predetermined angle of non-zero that is determined in each cell with respect to the direction perpendicular to the board 4. Each relatively positional relationship is determined according to the position on the board 4 in which the corresponding light emitting element 25 is disposed.

Then a determination whether the mounting of the lens 22 is completed to all the light emitting elements 25 mounted on the board 4 is made in Step S130. When the mounting of the lens 22 is not completed to all the light emitting elements 25 (NO in Step S130), the processes from Step S110 are repeated.

Figure 13E:
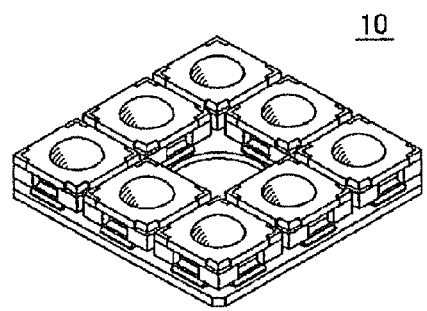

On the other hand, when the mounting of the lens 22 is completed to all the light emitting elements 25 (YES in Step S130), the illumination unit 10 is inspected in Step S132. When the determination that the illumination unit 10 is non-defective is made in the inspection, the illumination unit 10 is shipped as a completed product. FIG. 13E illustrates the state in which the illumination unit 10 is assembled.

<G. Action and Effect>

According to the first embodiment, the common light emitting element, seating, lens are mounted on the common board with the arbitrary relatively positional relationship, so that the many variations (product group) having different specifications of the illumination visual fields and work distances (WD) can be lined up while the cost is controlled.

[Second Embodiment]

In the first embodiment, after the light emitting element and the seating are individually fixed to the board, the position in which the lens is fixed is deviated with respect to the seating, thereby aligning the relatively positional relationship between the light emitting element and the lens. On the other hand, in a second embodiment of the invention, the relatively positional relationship of the seating with respect to the light emitting element is aligned using the seating to which the lens can be fixed with a specific positional relationship.

<A. Entire Device Configuration>

Because a visual sensor of the second embodiment has a configuration similar to that of the visual sensor of the first embodiment illustrated in FIG. 1, the detailed description is not repeated.

<B. Illumination Unit Structure>

Because the illumination unit 10 of the second embodiment has a configuration similar to that of the illumination unit of the first embodiment illustrated in FIG. 2, the detailed description is not repeated. However, a cell 3 is used instead of the cell 2.

<C. Cell Structure>

Figure 14:
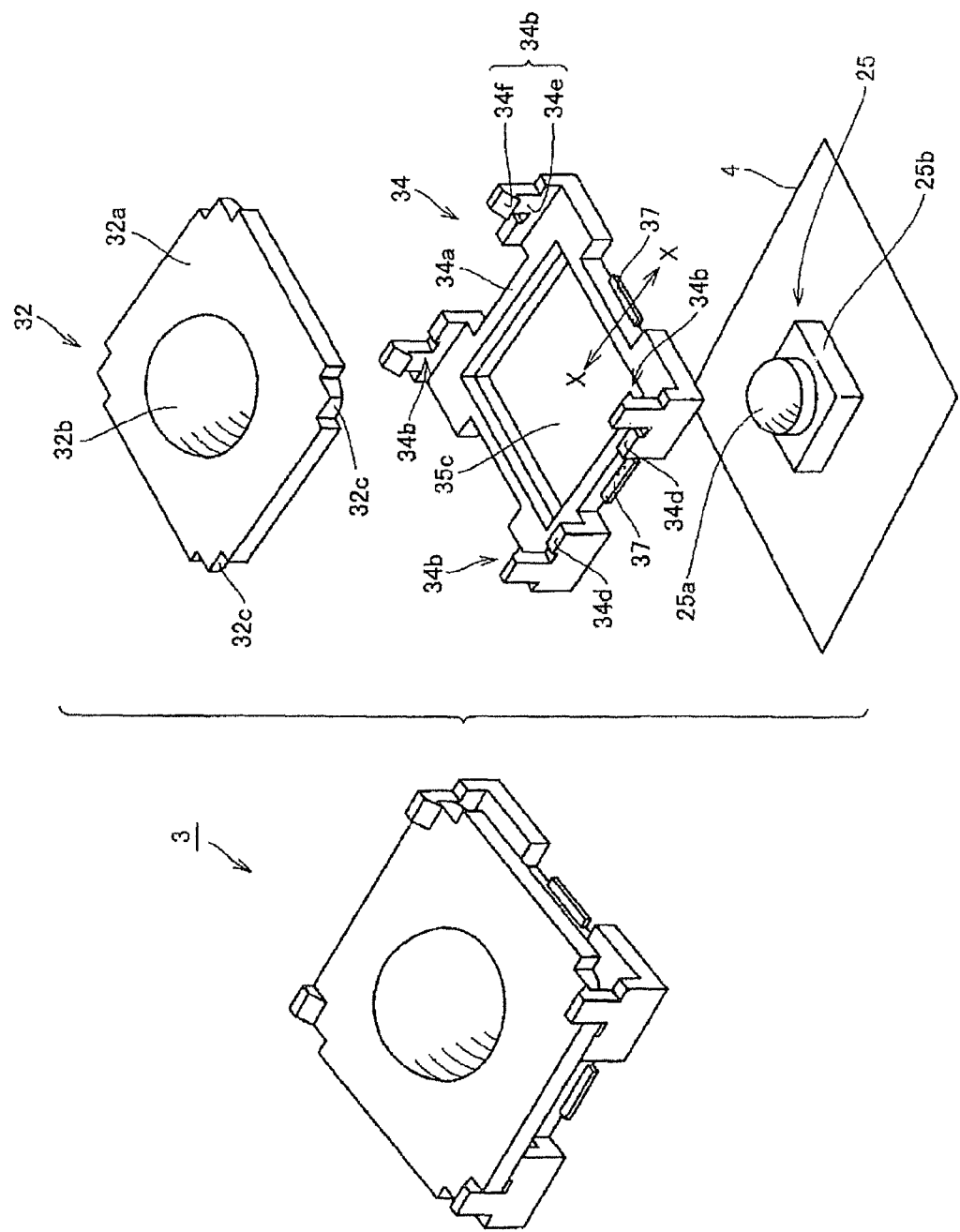
FIG. 14 is an exploded view of a cell constituting an illumination unit according to a second embodiment of the invention.

FIG. 14 is an exploded view of the cell 3 constituting an illumination unit 10 of the second embodiment. Referring to FIG. 14, the cell 3 includes a lens 32, a seating 34, and the light emitting element 25. The lens 32 and the seating 34 are fixed by engagement of a "pawl-shaped" member described later. The seating 34 and the board 4 are joined by a bonding agent 37.

The light emitting element 25 is mounted on the board 4. Because the mounting mode of the light emitting element 25 is similar to that of the cell 2 of the first embodiment, the detailed description is not repeated.

The seating 34 includes a bottom portion 34a having a square frame shape, and the seating 34 is disposed so as to surround the light emitting element 25 mounted on the board 4. That is, the seatings 34 are mounted on the board 4 as many as the light emitting elements 25 mounted on the board 4. Each seating 34 corresponds to one of the light emitting elements 25 mounted on the board 4. The bonding agent 37 is applied in a proper portion on the board 4 to fix the seating 34.

In the second embodiment, the seating 34 is disposed relative to the corresponding light emitting element 25 according to the relatively positional relationship that is determined according to the position on the board 4 in which the corresponding light emitting element 25 is disposed. That is, the seating 34 is aligned with the light emitting element 25. The detailed description is made later. The size (area) of an opening 34c of the seating 34 is larger than the sectional area of the light emitting element 25 such that the seating 34 can be aligned.

Retaining portions 34b are formed in the seating 34 in order to retain the corresponding lens 32 by a snap-fit method. The retaining portions 34b are disposed at four corners of a bottom portion 34a. The retaining portion 34b includes a base 34e, a tapered portion 34f, and a support portion 34d. The base 34e is extended from the bottom portion 34a toward the direction perpendicular to the board 4. The tapered portion 34f is formed so as to be extended from the leading end of the base 34e toward the inside of the bottom portion 34a. The support portion 34d is extended in the same direction as the base 34e from the bottom portion 34a to the middle of the base 34e. When the lens 32 is pushed from the upper side into the lower side along the direction perpendicular to the board 4 in FIG. 14, the base portion 32a of the lens 32 presses the tapered portion 34f to deform each retaining portion 34b toward the outside of the bottom portion 34a. When the lens 32 is further pushed, the lower surface of the base portion 32a abuts on the upper surface of the support portion 34d. The tapered portion 34f is formed up to a level where the upper surface of the base portion 32a is located while the lower surface of the base portion 32a is in contact with the support portion 34d. Therefore, when the lens 32 is pushed to an extent in which the lens 32 comes into contact with the support portion 34d, the contact of the tapered portion 34f with the side face of the base portion 32a is eliminated to return each retaining portion 34b to the inside of the bottom portion 34a. Therefore, the tapered portion 34f and the support portion 34d grasp the four corners of the base portion 32a to control the movement of the lens 32 in the direction perpendicular to the board 4.

A distance between the retaining portions 34b disposed in the same side is configured so as to be matched with a distance between a pair of notches 32c formed in the base portion 32a. That is, the lens 32 is mounted such that the notches 32c of the base portion 32a come into contact with the side faces of the bases 34e of the retaining portions 34b disposed on both sides, thereby controlling the movement of the lens 32 in an X-X direction. Therefore, the lens 32 is fixed to the seating 34.

In the retaining portion 34b of the seating 34, the lens 32 retained by the retaining portion 34b is configured to be able to maintain the predetermined relatively positional relationship with the seating 34.

The lens 32 is fixed to the seating 34 to output the illumination light generated in the light emitting element 25 to the outside. The lenses 32 are disposed as many as the light emitting elements 25 mounted on the board 4, and each lens 32 pairs with one of the light emitting elements 25. In the lens 32, the base portion 32a and a translucent convex lens portion 32b are integrally formed. The incoming light mainly from light emitting element 25 converges through the convex lens portion 32b. Although both the base portion 32a and the convex lens portion 32b may have the translucency, the light from the light emitting element 25 is positioned so as to be mainly transmitted through the convex lens portion 32b.

As described above, because the seating 34 (and the lens 32 fixed to the seating 34) is disposed while deviated (biased) from the center axis of the light emitting element 25 by the predetermined distance, the section in the convex lens portion 32b of the lens 32, that is, the translucent section of the lens 32 is larger than the light emitting section of the corresponding light emitting element 25.

In the cell 3 of the second embodiment, the illumination unit 10 having the desired illumination visual field and WD is provided by properly setting the relatively positional relationship between the seating 34 (and the lens 32 fixed to the seating 34) and the light emitting element 25. That is, in each cell 3, the seating 34 (and the lens 32 fixed to the seating 34) and the corresponding light emitting element 25 are disposed with the relatively positional relationship in which the light from the light emitting element 25 is output to the outside with the non-zero angle determined in each cell with respect to the direction perpendicular to the board 4.

Therefore, the bottom portion 34a of the seating 34 is designed with a margin according to the maximum alignment amount with respect to the mounting area of the light emitting element 25 such that the seating 34 can be aligned with the light emitting element 25. That is, an opening area of the bottom portion 34a is larger than the mounting area of the light emitting element 25.

The size of the bottom portion 34a of the seating 34 is designed as described above, which allows the seating 34 (and the lens 32 fixed to the seating 34) to be positioned with respect to the light emitting element 25 such that the desired relatively positional relationship is obtained.

<D. Adjustment by Alignment>

FIG. 15 is a view for explaining alignment in the illumination unit 10 of the second embodiment. FIG. 15A illustrates a state in which the seating 34 (and the lens 32 fixed to the seating 34) is positioned such that the optical axis Ax1 in the light irradiation direction of the light emitting element 25 is aligned with the optical axis Ax2 in the center of the lens 32. FIG. 15B illustrates a state in which the seating 34 (and the lens 32 fixed to the seating 34) is disposed while deviated to the right by a predetermined distance with respect to the state illustrated in FIG. 15A.

As described above, the relatively positional relationship between the lens 32 and the seating 34 is previously determined in the cell 3 of the second embodiment, and the relatively positional relationship of the seating 34 with respect to the light emitting element 25 is adjusted (seating alignment) to provide the variations of the WDs and the illumination visual fields of the illumination light output from the illumination unit 10.

More specifically, as illustrated in FIG. 15A, when the optical axis Ax1 of the light emitting element 25 is aligned with the optical axis Ax2 of the lens 32, illumination light B1 generated by the light emitting element 25 propagates along optical axis Ax1. At this point, because the optical axis Ax2 of the lens 32 exists on the same straight line as the optical axis Ax1, the illumination light B1 passing through the lens 32 is output as illumination light B2 while the propagation direction of the illumination light B1 is retained.

On the other hand, as illustrated in FIG. 15B, when the optical axis Ax2 of the lens 32 fixed to the seating 34 is deviated from the optical axis Ax1 of the light emitting element 25 while the seating 34 is aligned, the propagation direction of the illumination light B1 generated by the light emitting element 25 is changed after the illumination light B1 is incident to the lens 32. Because the illumination light B1 incident to the lens 32 converges toward the center axis of the lens 32, the resultant illumination light B2 is output in the direction in which the illumination light B2 is inclined with respect to the optical axis Ax1 of the light emitting element 25 by a predetermined angle of non-zero. Because the optical axes Ax1 and Ax2 are perpendicular to the board 4, the illumination light B2 output to the outside from the illumination unit 10 propagates with the non-zero angle that is determined in each cell with respect to the direction perpendicular to the board 4.

As illustrated in FIG. 15, the propagation direction of the illumination light B2 output from the illumination unit 10 is inclined to the same direction as the alignment direction of the seating 34. That is, in each cell 3, the seating 34 is disposed while deviated to the direction in which the light from the light emitting element 25 should be output with respect to the state in which the seating 34 is positioned to the optical axis Ax1 in the light irradiation direction of the corresponding light emitting element 25. The output direction of the illumination light B2 is largely inclined with respect to the optical axis Ax1 with increasing alignment amount (displacement amount) of the seating 34.

The desired illumination visual field and WD can be realized by performing the alignment of the seating 34 in the proper displacement direction and with the proper displacement amount. In other words, various alignment directions and alignment amounts are set while the same light emitting element 25, lens 32, and seating 34 are used, which allows the illumination unit 10 having various illumination visual fields and WDs to be provided. Accordingly, it is not necessary that the light emitting elements 25, the lenses 32, and the seatings 34 be individually designed as many as the variations of the illumination visual fields and WDs, which allows the production cost to be reduced.

Because the whole design of the illumination unit 10 is similar to that illustrated in FIGS. 6 to 8, the detailed description is not repeated.

<E. Adjustment by Lens Shape>

As illustrated in the first embodiment, the variations of the more kinds of illumination visual fields and work distances (WD) can be provided by preparing the plural kinds of lenses 32 having different shapes.

Because the description of principle is similar to that illustrated in FIG. 9, the detailed description is not repeated.

Particularly, in the second embodiment, the retaining portion 34b of the seating 34 is formed into the "snap-fit" shape, so that the lens 32 can easily be mounted. Therefore, the illumination visual field can easily be changed by preparing the plural lens groups in which the shapes of the convex lens portions 32b differ from one another while the sizes of the base portions 32a are unified. Therefore, the product group having more variations can be provided while the cost is controlled.

A semifinished product in which only the light emitting element 25 and the seating 34 are mounted on the board 4 is previously produced, and the lens 32 is mounted on the previously-prepared semifinished product according to the required illumination visual field and WD at the time of an order from a customer, which allows rapid and sophisticated support to a customer request while the cost is controlled.

<F. Producing Process>

Figure 16:
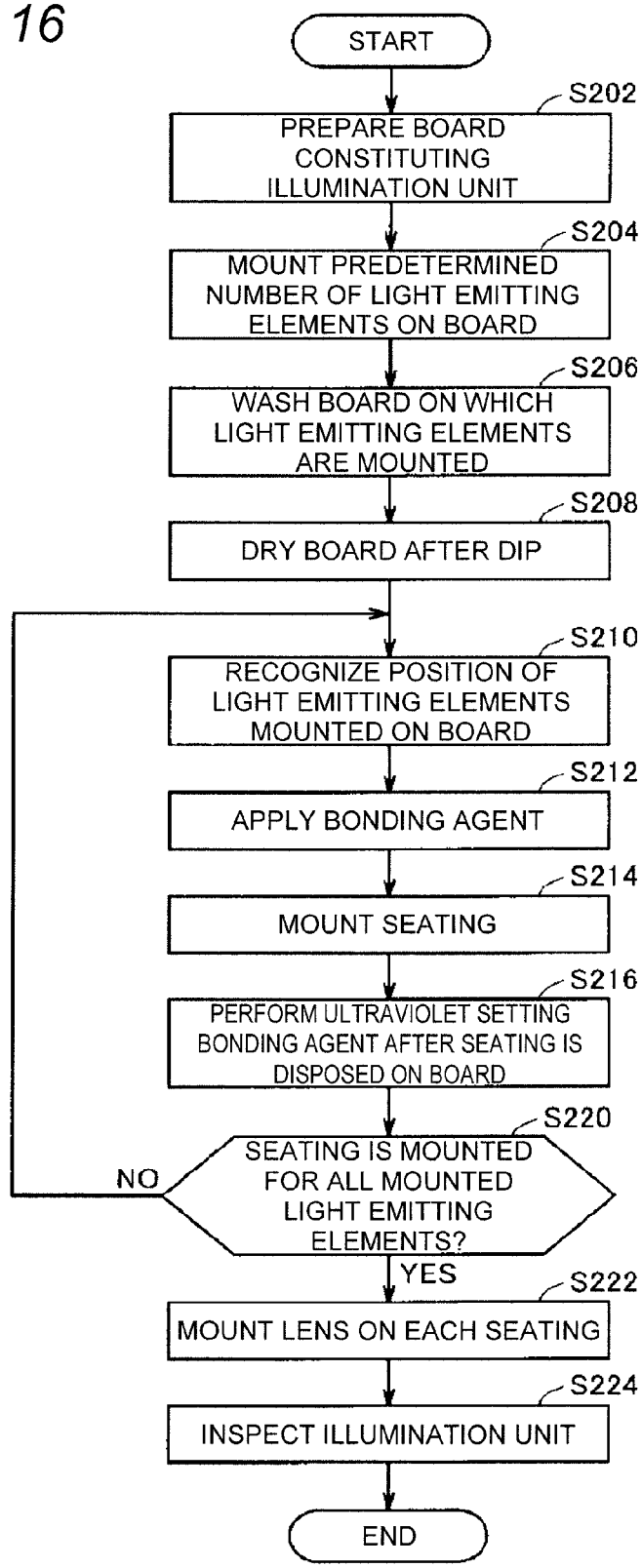
FIG. 16 is a flowchart illustrating a process of producing the illumination unit of the second embodiment.
Figure 17:
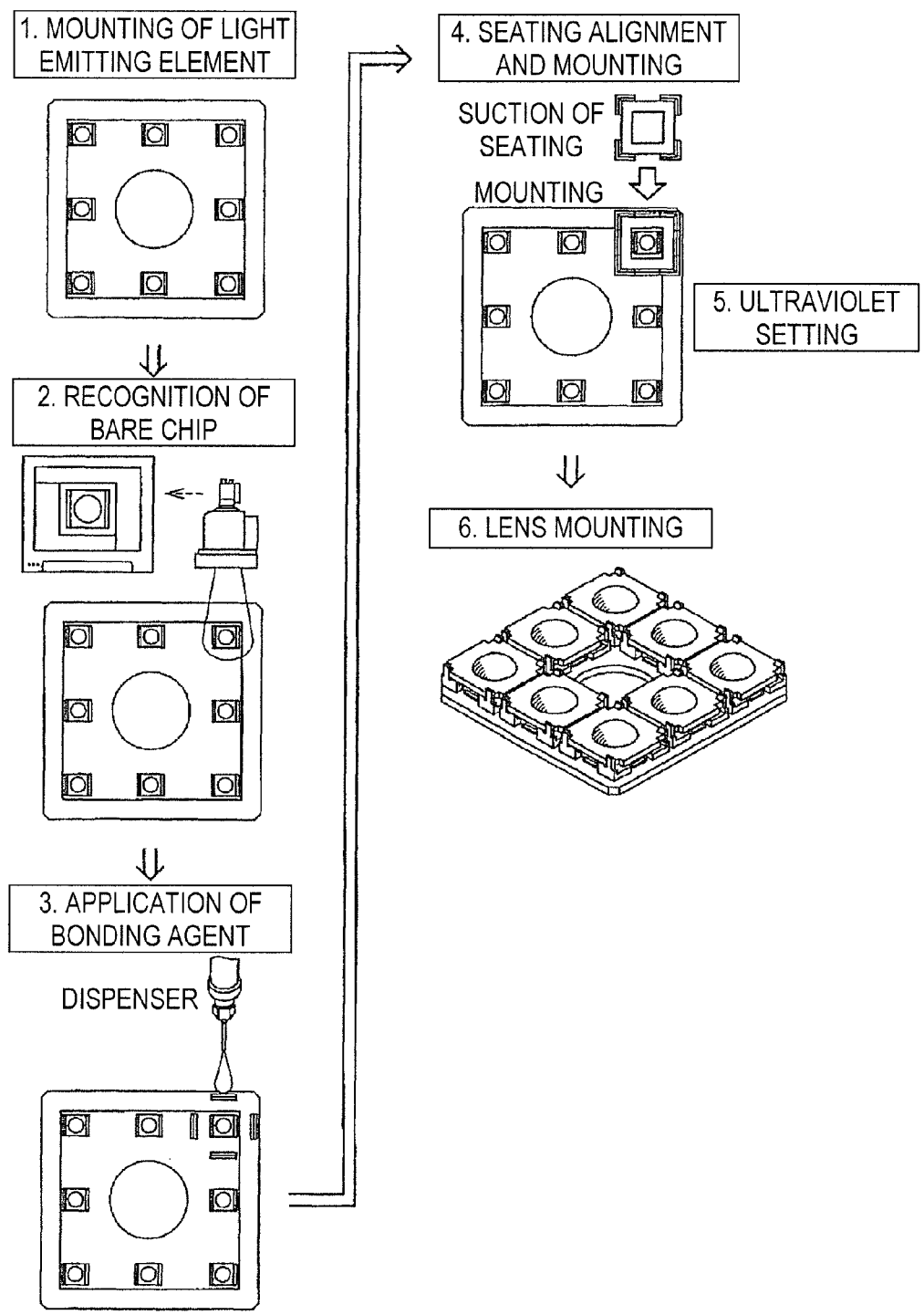
FIG. 17 is a schematic diagram illustrating the process of producing the illumination unit of the second embodiment.

FIG. 16 is a flowchart illustrating a process of producing the illumination unit 10 of the second embodiment. FIG. 17 is a schematic diagram illustrating the process of producing the illumination unit 10 of the second embodiment. FIG. 18 is a view for explaining each state during the production of the illumination unit 10 of the second embodiment.

Referring to FIG. 16, in Step S202, the board 4 constituting the illumination unit 10 is prepared. In Step S204, the predetermined light emitting elements 25 are mounted on the prepared board 4. Typically, the light emitting elements 25 are collectively or sequentially mounted in predetermined positions on the prepared board 4 by the well-known surface mounting method. Therefore, the plural light emitting elements 25 are mounted on the board 4 such that the light irradiation direction of each light emitting element 25 is substantially perpendicular to the board 4.

Figure 18A:
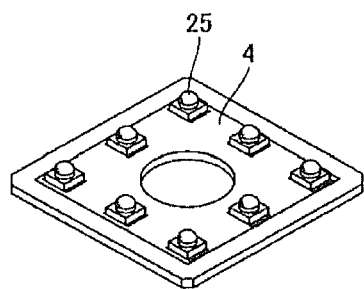
FIGS. 18A to 18E are views for explaining each state during the production of the illumination unit of the second embodiment.

In Step S206, the board 4 on which the light emitting elements 25 are mounted is washed (typically, the dipping treatment in the isopropyl alcohol solution). In Step S208, the board 4 is dried in the constant-temperature oven after the dip. The board 4 illustrated in a process of "1. mounting of light emitting element" of FIG. 17 is obtained after Step S208 is performed. FIG. 18A illustrates the board 4 in the state in which the eight light emitting elements 25 are mounted.

When the board 4 in the state in which the eight light emitting elements 25 are mounted is obtained through the process, the flow goes to a process of mounting the seatings 34 from Step S210.

In Step S210, the positions in which the light emitting elements 25 are mounted on the board 4 are recognized. This is because the light emitting element 25 mounted on the board 4 is not always mounted on the board 4 with the same positional relationship. More specifically, as illustrated in a process of "2. recognition of bare chip" of FIG. 17, the position of the bare chip (the light emitting element 25 in the state in which an exterior package and the like are not attached to the light emitting element 25) is specified using the well-known image processing technique.

Figure 18B:
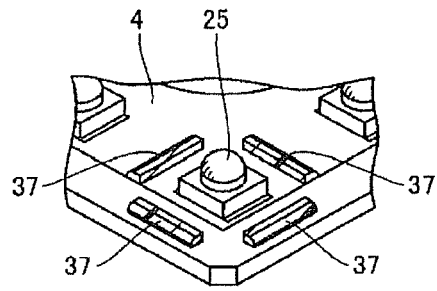

In Step S212, the bonding agent 37 is applied in the range that is determined according to the position of the light emitting element 25 specified on the board 4. At this point, as illustrated in a process of "3. application of bonding agent" of FIG. 17, the predetermined amount of bonding agent 37 is applied after the well-known dispenser (the apparatus that quantitatively ejects the liquid) is positioned according to the image recognition result. FIG. 18B illustrates the board 4 in the state in which the bonding agent 37 is applied to the four sides surrounding the light emitting element 25.

In Step S214, the seating 34 is mounted on the target light emitting element 25 so as to have the predetermined relatively positional relationship corresponding to the position. That is, as illustrated in FIG. 6, the seating 34 is positioned based on the corresponding light emitting element 25 such that the alignment amount is generated according to the position on the board 4. More specifically, as illustrated in a process of "4. seating alignment and mounting" of FIG. 17, the seating 34 is positioned in the intended relative position while sucked with the well-known robot apparatus.

Figure 18C:
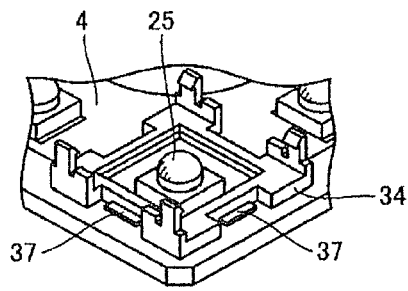

In Step S216, the ultraviolet curing of the bonding agent 37 is performed when the seating 34 is disposed in the board 4. More specifically, as illustrated in a process of "5. UV curing" of FIG. 17, the bonding agent 37 is irradiated with a predetermined amount of ultraviolet ray using the well-known ultraviolet irradiation apparatus. FIG. 18C illustrates the state in which the seating 34 is mounted so as to surround the light emitting element 25.

In the process between Steps S214 and S216, the pre-annealing treatment (heat treatment) may be performed in order to stabilize the seating 34 and the bonding agent 37.

The mounting of the seating 34 is completed in one cell 3 through the processes in Steps S210 and S216. That is, in the processes in Steps S210 to S216, each of the plural seatings 34 is fixed onto the board 4 so as to correspond to one of the plural light emitting elements 25. The relatively positional relationship between each seating 34 and the corresponding light emitting element 25 is determined such that the light is emitted outward from the light emitting element 25 through the corresponding lens 32 with the non-zero angle that is determined in each cell with respect to the direction perpendicular to the board 4. Each relatively positional relationship is determined according to the position on the board 4 in which the corresponding light emitting element 25 is disposed.

A determination whether the mounting of the seating 34 is completed to all the light emitting elements 25 mounted on the board 4 is made in Step S220. When the mounting of the seating 34 is not completed to all the light emitting elements 25 (NO in Step S220), the processes from Step S210 are repeated.

Figure 18D:
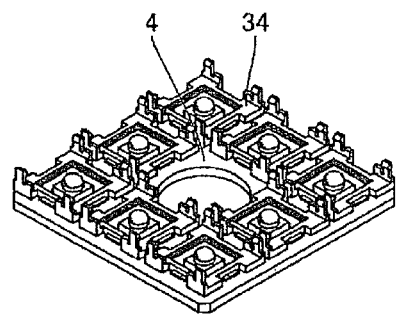
Figure 18E:
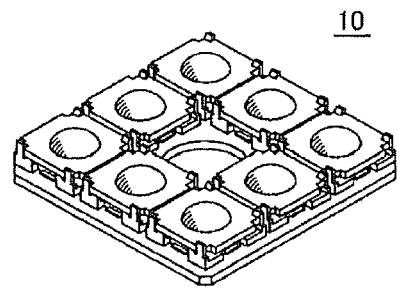

On the other hand, when the mounting of the seating 34 is completed to all the light emitting elements 25 (YES in Step S220), the lens 32 is mounted on the seating 34 (Step S222). More specifically, as illustrated in a process of "6. mounting of seating" of FIG. 17, the desired lenses are sequentially mounted on the retaining portion 34b of the seating 34 retaining portion 34b by man power or the well-known robot apparatus. That is, the lenses 32 are fixed onto the seatings 34, respectively, such that each lens 32 corresponds to one of the seatings 34. FIG. 18D illustrates the state in which all the seatings 34 are mounted, and FIG. 18E illustrates the state in which the lens 32 is mounted on each seating 34.

In Step S224, the illumination unit 10 is inspected. When the determination that the illumination unit 10 is non-defective is made in the inspection, the illumination unit 10 is shipped as the completed product.

<G. Action and Effect>

According to the second embodiment, the common light emitting element, seating, and lens are mounted on the common board with the intended relatively positional relationship, so that the many variations (product group) having different specifications of the illumination visual fields and work distances (WD) can be lined up while the cost is controlled.

Particularly, according to the second embodiment, the necessary lenses can be mounted after the seatings are mounted, so that the working process can be simplified while the variations are increased in an after-the-fact manner.

[Third Embodiment]

In the first and second embodiments, the lens and the seating are individually mounted as an independent component with respect to the light emitting element 25. Alternatively, the lens and the seating may integrally be formed. In such cases, a component in which the lens and the seating are integrated is positioned with respect to the light emitting element.

Because other configurations and producing methods are similar to those of the first and second embodiments, the detailed description is not repeated.

[First Modification of First to Third Embodiments]

In each cell of the first to third embodiments, a lens including a reflecting surface may be used in at least part of the surface on the side to which the light is incident from the light emitting element 25.

Figure 20:
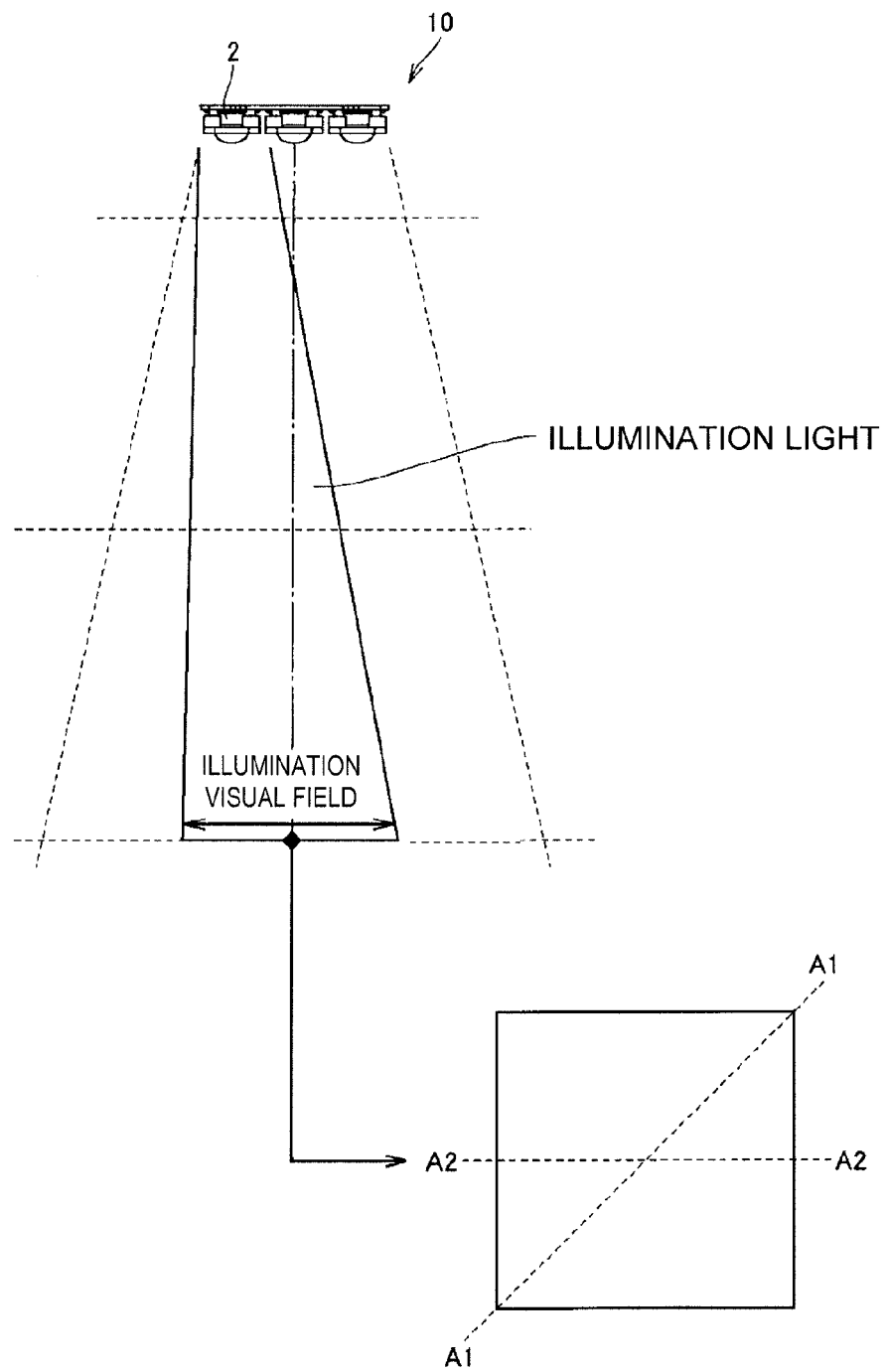
FIG. 20 is a view for explaining an illumination intensity improvement effect by the lens of the first modification.

FIG. 19 is a sectional view illustrating a structure of a lens according to a first modification of the embodiments. FIGS. 20 and 21 are views for explaining an illumination intensity improvement effect by the lens of the first modification. FIG. 22 is a view for explaining an irradiation pattern improvement effect by the lens of the first modification.

FIG. 19A illustrates a sectional structure of the lens 22 of the first embodiment, and FIG. 19B illustrates a sectional structure of the lens 22# of the first modification.

As illustrated in FIG. 19B, in the lens 22# of the first modification, the base portion 22a is formed into a shape in which the base portion 22a is further swelled toward the side of the light emitting element 25 than the lens 22, and the illumination light generated by the light emitting element 25 is further guided to a radiant surface. Particularly, in the lens 22#, a reflecting surface 22e is formed in a surface on the side to which the light is incident from the light emitting element 25. Typically, the reflecting surface 22e is an aluminum mirror formed by a method such as aluminum vapor deposition. Preferably the reflecting surface 22e is mirror-polished such that normal reflection is generated. Obviously any well-known technique can be used in a material and production method of the reflecting surface 22e.

Referring to FIG. 19, the improvement of the illumination intensity by the use of the lens 22# of the first modification will be described below.

As illustrated in FIG. 19A, in a structure in which the reflecting surface 22e is not provided, the illumination light that is emitted from the light emitting element 25 with the relatively small outgoing angle impinges on the convex lens portion 22b, and the object OBJ is irradiated with the illumination light as the illumination light B1. On the other hand, the illumination light that is emitted from the light emitting element 25 with the relatively large outgoing angle cannot impinge on the convex lens portion 22b, and the illumination light is output to the outside from a portion different from the outgoing surface of the lens 22 (numeral B12), or the illumination light is attenuated in the lens 22. Therefore, the object OBJ can be irradiated only with part of the illumination light generated by the light emitting element 25.

On the other hand, as illustrated in FIG. 19B, in the structure in which the reflecting surface 22e is provided, even if the illumination light is emitted from the light emitting element 25 with the relatively large outgoing angle, the illumination light impinges on the reflecting surface 22e after being reflected by an interface on the outgoing surface side of the base portion 22a. The illumination light reflected by the reflecting surface 22e propagates through the base portion 22a, and the illumination light is output to the outside from the outgoing surface side (numeral B13).

Therefore, the object OBJ can be irradiated with the large amount of illumination light generated by the light emitting element 25. Accordingly, the use of the lens 22# can enhance the intensity of the illumination light even if the same light emitting element 25 is used.

Figure 21A:
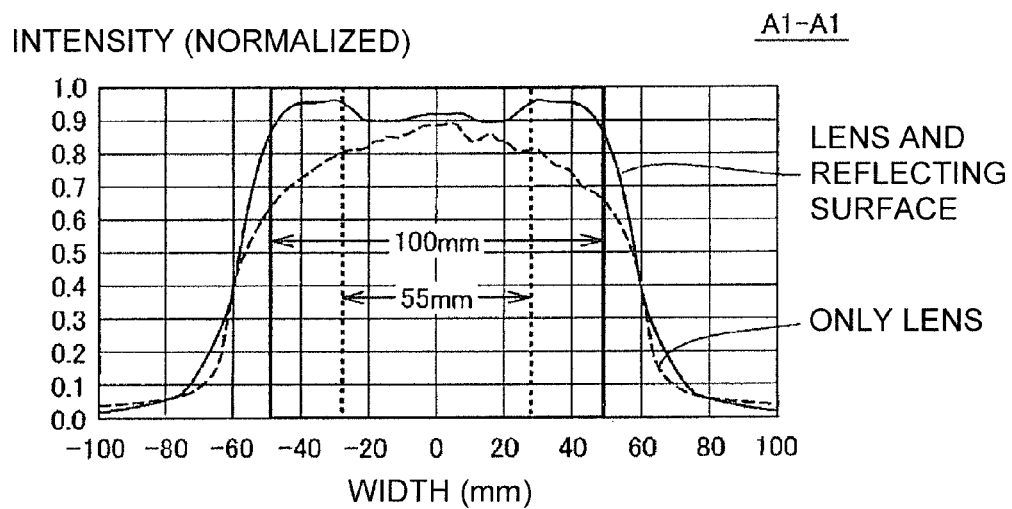
FIGS. 21A and 21B are views for explaining the illumination intensity improvement effect by the lens of the first modification.
Figure 21B:
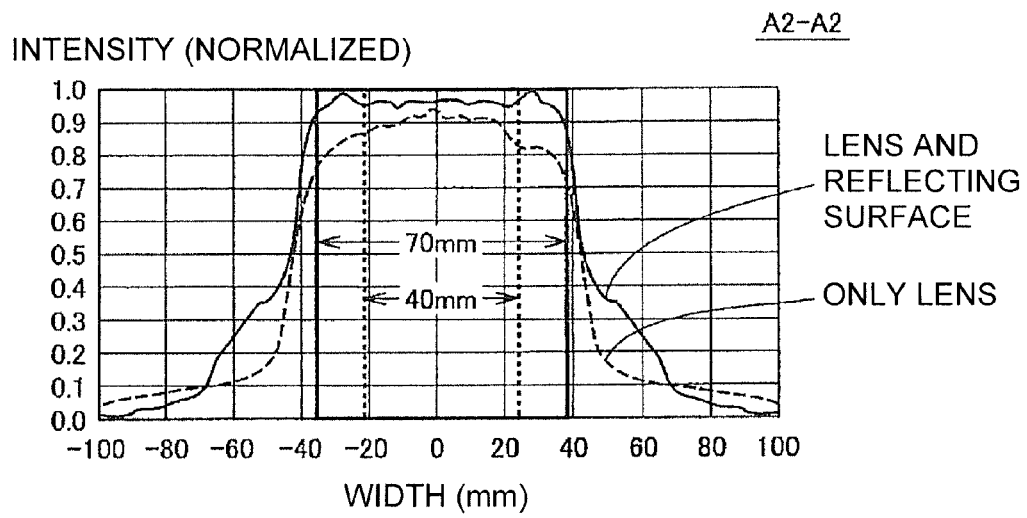

FIG. 21 illustrates comparison result of an illumination intensity profile within the illumination visual field irradiated with a certain cell 2 as illustrated in FIG. 20. FIG. 21A illustrates the illumination intensity profile on a diagonal line A1-A1 of the illumination visual field illustrated in FIG. 20, and FIG. 21B illustrates the illumination intensity profile on an opposite side A2-A2 of the illumination visual field illustrated in FIG. 20. The illumination intensity profiles are computed by the computer simulation. In FIG. 21, "only lens" indicates the profile when the lens 22 that does not include the reflecting surface 22e illustrated in FIG. 19A is used, and "lens and reflecting surface" indicates the profile when the lens 22# that includes the reflecting surface 22e illustrated in FIG. 19B is used.

In addition to the illumination intensity profiles, FIG. 19A illustrates a range where 90% of in-plane evenness (a ratio of intensity in each portion to maximum intensity) can be secured in the illumination visual field.

As illustrated in FIG. 19A, in the diagonal line A1-A1, 90% of in-plane evenness can be secured in the range of 55 mm when the lens 22 is used. On the other hand, 90% of in-plane evenness can be secured in the range of 100 mm when the lens 22# is used. As illustrated in FIG. 19B, in the opposite side A2-A2, 90% of in-plane evenness can be secured in the range of 40 mm when the lens 22 is used. On the other hand, 90% of in-plane evenness can be secured in the range of 70 mm when the lens 22# is used.

That is, when the lens 22# including the reflecting surface 22e is used, a region where 90% of in-plane evenness can be secured is expanded about 1.8 times the illumination intensity profile in the case where the lens 22 that does not include the reflecting surface 22e is used. Therefore, the use of the lens 22# including the reflecting surface 22e improves the in-plane evenness.

For example, it is considered that the in-plane evenness is secured in the specific illumination visual field. When the lens 22 that does not include the reflecting surface 22e is used, as illustrated in FIG. 22A, it is necessary to secure the in-plane evenness in the measurement visual field by preparing a pattern in which the pieces of illumination light output from the cells 2 are overlapped with one another in the measurement visual field. That is, when the lens 22 that does not include the reflecting surface 22e is used, because the range where the in-plane evenness can be secured is relatively narrow as described above, it is necessary to overlap the plural pieces of illumination light. Therefore, because the outside of the intended measurement visual field is irradiated with the illumination light, illumination efficiency is inevitably degraded.

On the other hand, when the lens 22# including the reflecting surface 22e is used, the range where the in-plane evenness can be secured is relatively widened as illustrated in FIG. 22B, the illumination visual field of each cell 2 can substantially be matched with the measurement visual field. That is, only the intended measurement visual field is irradiated with the illumination light output from each cell 2, so that the illumination efficiency can be enhanced. According to the simulation result, in the example illustrated in FIG. 22, the use of the lens 22# including the reflecting surface 22e can improve the illumination efficiency (illumination intensity) about 1.5 times the case where the lens 22 that does not include the reflecting surface 22e is used.

Figure 23:
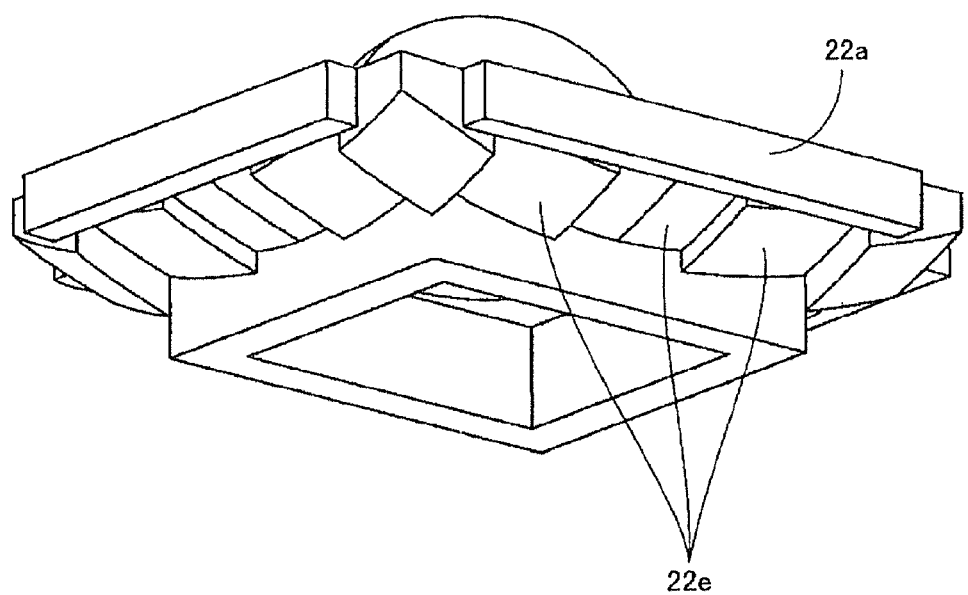
FIG. 23 is a perspective view illustrating an example of the lens of the first modification.

The reflecting surface 22e of the lens 22# of the first modification may be formed as plural reflecting regions disclosed in Japanese Unexamined Patent Publication No. 2006-222413. FIG. 23 illustrates an example of the lens in which the plural reflecting regions are formed.

In the lens illustrated in FIG. 23, the plural reflecting surfaces 22e are formed in each predetermined partition on the board side of the base portion 22a. The light emitted from the light emitting element 25 is reflected by the reflecting surfaces 22e, and the light is output to the front face side of the lens 22.

According to the first modification, because the object OBJ can efficiently be irradiated with the illumination light, the illumination intensity can be enhanced. The enhancement of the illumination intensity (illumination efficiency) improves the measurement accuracy and realizes the necessary illumination intensity with a less electric power amount, so that the power consumption and the heat generation can be suppressed.

[Second Modification of First to Third Embodiments]

Figure 24C:
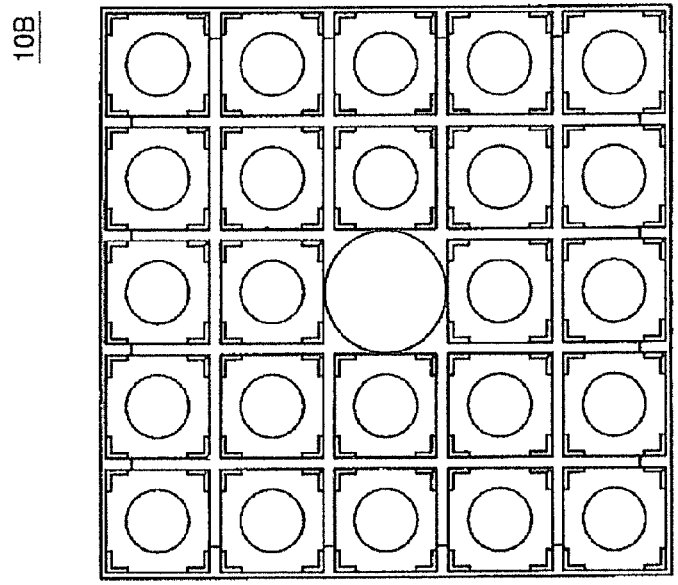
FIGS. 24A to 24C illustrate a schematic configuration of an illumination unit according to a second modification of the embodiments.
Figure 24B:
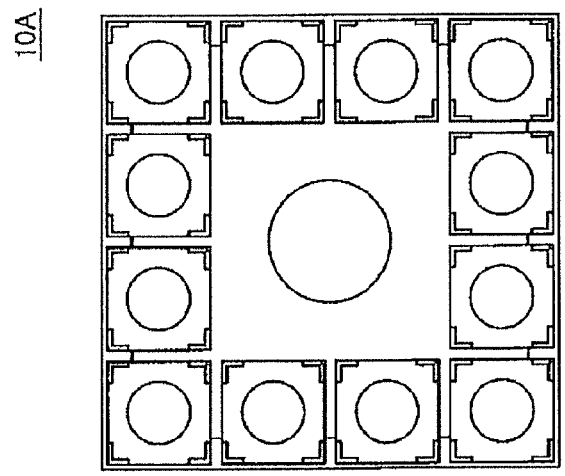
Figure 24A:
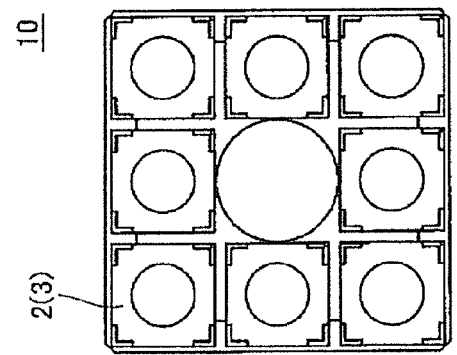

FIG. 24 illustrates a schematic configuration of an illumination unit according to a second modification of the embodiments. As illustrated in FIG. 24, when the variations are lined up for the intended illumination visual field and work distance (WD), occasionally it is necessary to adjust the necessary whole light amount. That is, the illumination intensity per unit area is decreased with increasing illumination visual field. Therefore, not only the illumination unit 10 in which the 8 cells are disposed as illustrated in FIG. 24A, but also an illumination unit 10A in which the 12 cells are disposed as illustrated in FIG. 24B and an illumination unit 10B in which the 24 cells are disposed as illustrated in FIG. 24C may be formed in order to secure the necessary illumination intensity.

A pattern in which the cells are disposed can appropriately be designed according to the state of the object OBJ of the measurement target or an installation status of the object OBJ. Particularly, the cells of the second modification are formed independently of one another, so that the cell can be mounted on the board without a particular restriction.

[Third Modification of First to Third Embodiments]

In the first to third embodiments, imaging unit 100 has illumination unit 10 and the imaging portion 50 integrated therein. Alternatively, the imaging unit 100 may be implemented while separated from the imaging portion 50.

Figure 25:
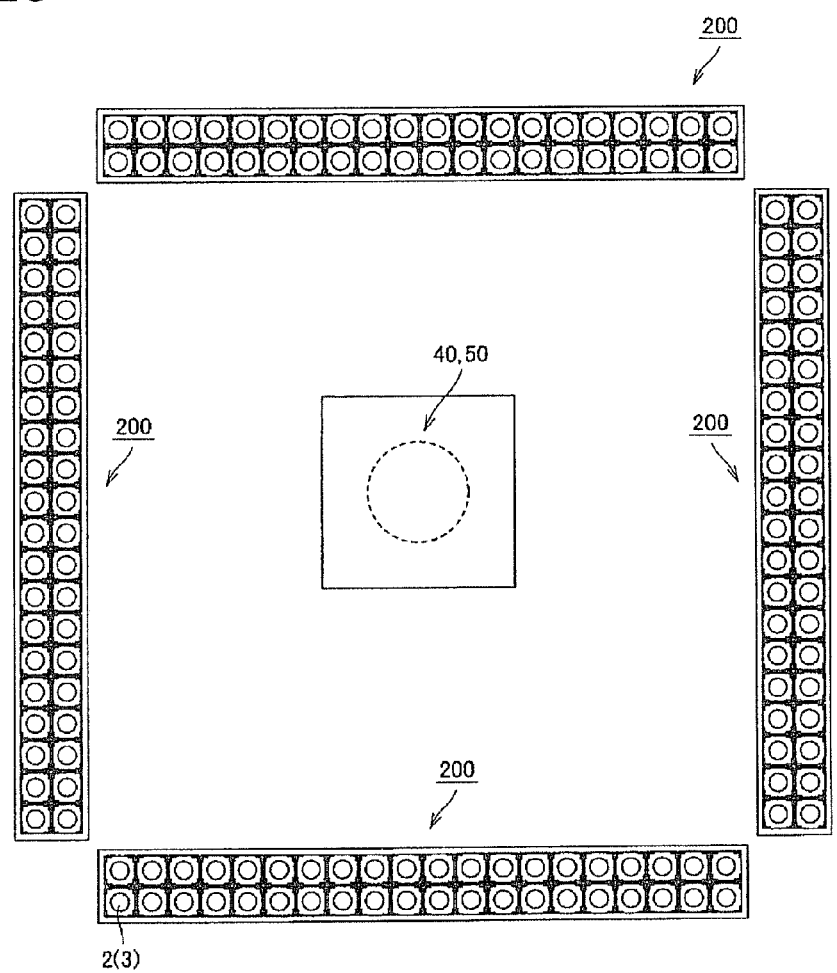
FIG. 25 illustrates an example of a disposition configuration of an illumination device according to a third modification of the embodiments.

For example, as illustrated in FIG. 25, the object OBJ may be illuminated using four illumination devices 200 in which the plural cells 2 are arrayed. That is, the illumination devices 200 are disposed in four directions while the lens unit 40 and the imaging portion 50 are disposed in the center, and the object OBJ is illuminated using the four illumination devices 200.

At this point, the alignment amount of each cell 2 included in each illumination device 200 is determined according to the relative position between the illumination device 200 and the object OBJ. Typically, in each illumination device 200, the amount and direction of the alignment are determined in each cell 2 such that a cross wise direction of the illumination device 200 in which the cell 2 is disposed is irradiated with the light. In the configuration of FIG. 25, the short-side side is irradiated with the larger amount of illumination light from each illumination device 200. Accordingly, the direction irradiated with the larger amount of illumination light is aligned with the side on which the object OBJ is disposed, which allows the object OBJ to be properly irradiated.

Figure 26:
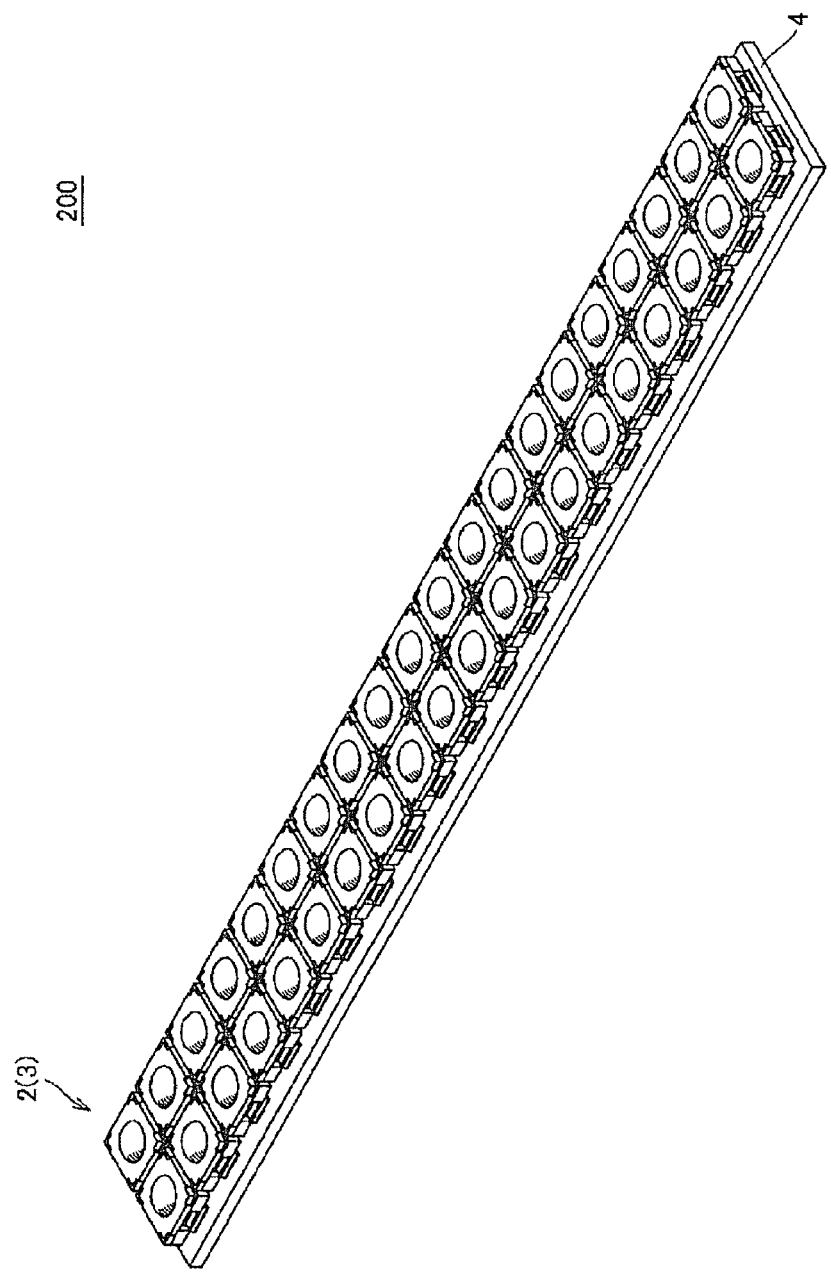
FIG. 26 is a perspective view of the illumination device of the third modification.

FIG. 26 is a perspective view of the illumination device of the third modification. Referring to FIG. 26, the illumination device 200 of the third modification includes plural cells 2 that are disposed in two lines on the board 4. Because the configuration of each cell 2 is similar to that of the first embodiment, the detailed description is not repeated.

The disclosed embodiments are illustrated only by way of example, and the invention is not limited to the embodiments. The scope of the invention is expressed by not the above description, but claims of the invention. It is intended that the invention includes the meaning equivalent to claims of the invention and all changes within the scope of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An illumination device comprising:
   a board;
   a plurality of light emitting elements that are mounted on the board, the plurality of light emitting elements being disposed such that a light irradiation direction of each light emitting element becomes substantially perpendicular to the board; and
   a plurality of lenses,
   wherein each of the plurality of lens is paired with one of the plurality of light emitting elements, and
   wherein a relative positional relationship between the light emitting element and the lens in each pair varies according to a position on the board in which the corresponding light emitting element is disposed.

2. The illumination device according to claim 1, wherein an optical axis of the lens in each pair is disposed while deviated to a direction that the corresponding light emitting element should irradiate a light beam with respect to a position in which the optical axis is positioned to an axis in a light irradiation direction of the corresponding light emitting element.

3. The illumination device according to claim 1,
   wherein the board includes an opening through which a reflection light irradiated from the light emitting elements and reflected by an object are passed, and
   wherein the optical axis of the lens in each pair is disposed closer to the opening than the axis in the light irradiation direction of the corresponding light emitting element.

4. The illumination device according to claim 1,
   wherein the board includes an opening through which a reflection light irradiated from the light emitting elements and reflected by an object are passed, and
   wherein, in the two pairs that are symmetrically disposed in relation to the opening, a relative positional relationship in one of the pairs and a relative positional relationship in the other pair is symmetrical.

5. The illumination device according to claim 1, further comprising:
   seatings, each of the seatings corresponding to one of the plurality of light emitting elements,
   wherein each of the seatings includes a retaining portion that retains the corresponding lens.

6. The illumination device according to claim 5, wherein a translucent section of each of the lenses is larger than a light irradiation section of the corresponding light emitting element.

7. The illumination device according to claim 5,
   wherein each of the seating is mounted on the board with a relative positional relationship that is previously determined with respect to the corresponding light emitting element, and
   wherein the retaining portion retains the lens so that the relatively positional relationship of the lens retained by the retaining portion with respect to the seating is adjustable.

8. The illumination device according to claim 5,
   wherein the retaining portion retains the lens so that the lens is positioned with a predetermined relative positional relationship with respect to the seating, and
   wherein each of the seating is mounted on the board with a relative positional relationship that is predetermined according to a position on the board on which the corresponding light emitting element is mounted.

9. The illumination device according to claim 1, wherein the lens includes a reflecting surface in at least part of a surface on a side to which the light beam is incident from the light emitting element.

10. An illumination device producing method comprising the steps of:
    mounting a plurality of light emitting elements on a board such that a light irradiation direction of each light emitting element becomes substantially perpendicular to the board;
    mounting a plurality of seatings on the board such that each of the plurality of seatings corresponds to one of the plurality of light emitting elements; and
    fixing a plurality of lenses onto the seatings such that each of the plurality of lens corresponds to one of the plurality of seatings,
    wherein a relatively positional relationship between each lens and the corresponding light emitting element is determined according to a position on the board in which the light emitting element is disposed.

11. The illumination device producing method according to claim 10, wherein a relative positional relationship between each lens and the corresponding seating is determined according to a position on the board on which the seating is mounted in the fixing step.

12. The illumination device producing method according to claim 10, wherein a relative positional relationship between each seating and the corresponding light emitting element is determined according to a position on the board on which the light emitting element is mounted in the step of mounting the plurality of seatings.

13. The illumination device according to claim 2,
    wherein the board includes an opening through which a reflection light irradiated from the light emitting elements and reflected by an object are passed, and
    wherein the optical axis of the lens in each pair is disposed closer to the opening than the axis in the light irradiation direction of the corresponding light emitting element.

14. The illumination device according to claim 2,
    wherein the board includes an opening through which a reflection light irradiated from the light emitting elements and reflected by an object are passed, and
    wherein, in the two pairs that are symmetrically disposed in relation to the opening, a relative positional relationship in one of the pairs and a relative positional relationship in the other pair is symmetrical.

15. The illumination device according to claim 2, further comprising:

seatings, each of the seatings corresponding to one of the plurality of light emitting elements, wherein each of the seatings includes a retaining portion that retains the corresponding lens.

16. The illumination device according to claim 15, wherein a translucent section of each of the lenses is larger than a light irradiation section of the corresponding light emitting element.

17. The illumination device according to claim 15, wherein each of the seating is mounted on the board with a relative positional relationship that is previously determined with respect to the corresponding light emitting element, and wherein the retaining portion retains the lens so that the relatively positional relationship of the lens retained by the retaining portion with respect to the seating is adjustable.

18. The illumination device according to claim 15, wherein the retaining portion retains the lens so that the lens is positioned with a predetermined relative positional relationship with respect to the seating, and wherein each of the seating is mounted on the board with a relative positional relationship that is predetermined according to a position on the board on which the corresponding light emitting element is mounted.

19. The illumination device according to claim 1, wherein the lens includes a reflecting surface in at least part of a surface on a side to which the light beam is incident from the light emitting element.

* * * * *